United States Patent
Sun et al.

(10) Patent No.: US 8,903,483 B2
(45) Date of Patent: *Dec. 2, 2014

(54) DEVICES AND METHODS FOR MONITORING PHYSIOLOGICAL INFORMATION RELATING TO SLEEP WITH AN IMPLANTABLE DEVICE

(71) Applicant: NeuroPace, Inc., Mountain View, CA (US)

(72) Inventors: Felice Sun, Palo Alto, CA (US); Benjamin D Pless, Atherton, CA (US); Barbara Gibb, Foster City, CA (US)

(73) Assignee: NeuroPace, Inc., Mountain View, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 13/966,899

(22) Filed: Aug. 14, 2013

(65) Prior Publication Data

US 2013/0345522 A1 Dec. 26, 2013

Related U.S. Application Data

(60) Continuation of application No. 13/733,055, filed on Jan. 2, 2013, now Pat. No. 8,538,514, which is a continuation of application No. 13/274,037, filed on Oct. 14, 2011, now Pat. No. 8,369,940, which is a continuation of application No. 12/971,455, filed on Dec. 17, 2010, now Pat. No. 8,068,904, which is a division of application No. 11/704,451, filed on Feb. 9, 2007, now Pat. No. 7,894,890.

(51) Int. Cl.
| | |
|---|---|
| *A61B 5/048* | (2006.01) |
| *A61B 5/0478* | (2006.01) |
| *A61B 5/00* | (2006.01) |
| *A61B 5/11* | (2006.01) |
| *A61B 5/04* | (2006.01) |
| *A61N 1/36* | (2006.01) |
| *A61B 5/0452* | (2006.01) |
| *A61B 5/1455* | (2006.01) |
| *A61B 5/0205* | (2006.01) |
| *A61B 5/01* | (2006.01) |
| *A61B 5/026* | (2006.01) |
| *A61B 5/024* | (2006.01) |

(52) U.S. Cl.
CPC ............. *A61B 5/4812* (2013.01); *A61B 5/0478* (2013.01); *A61B 5/4815* (2013.01); *A61B 5/1118* (2013.01); *A61B 5/686* (2013.01); *A61B 5/04012* (2013.01); *A61B 5/11* (2013.01); *A61N 1/36082* (2013.01); *A61B 5/0452* (2013.01); *A61B 5/14551* (2013.01); *A61B 5/0205* (2013.01); *A61B 5/01* (2013.01); *A61B 5/02438* (2013.01); *A61B 5/026* (2013.01)
USPC ......................................... 600/544; 600/545

(58) Field of Classification Search
USPC .................................................. 600/544, 545
See application file for complete search history.

(56) References Cited

U.S. PATENT DOCUMENTS

| | | |
|---|---|---|
| 5,047,930 A | 9/1991 | Martens et al. |
| 5,280,791 A | 1/1994 | Lavie |

(Continued)

OTHER PUBLICATIONS

Guyton, A.C., "Textbook of Medical Physiology", 8th ed., Wonsiewicz M.J. ed., pp. wii-xli (Table of Contents only), 1991.

(Continued)

*Primary Examiner* — Joseph Dietrich

(74) *Attorney, Agent, or Firm* — Arent Fox LLP

(57) ABSTRACT

Described here are implantable devices and methods for monitoring physiological information relating to sleep. The implantable devices are generally designed to include at least one sensor for sensing physiological information, a processor for processing the physiological information using low computational power to detect a sleep stage, and a battery. The detected sleep stage information may then be used to indicate sleep quality, identify or monitor a medical condition, or guide treatment thereof.

18 Claims, 25 Drawing Sheets

(56) References Cited

U.S. PATENT DOCUMENTS

| | | | |
|---|---|---|---|
| 5,891,176 | A | 4/1999 | Bornzin |
| 6,006,124 | A | 12/1999 | Fischell et al. |
| 6,016,449 | A | 1/2000 | Fischell et al. |
| 6,473,639 | B1 | 10/2002 | Fischell et al. |
| 6,641,542 | B2 | 11/2003 | Cho et al. |
| 6,731,984 | B2 | 5/2004 | Cho et al. |
| 6,810,285 | B2 | 10/2004 | Pless et al. |
| 6,881,192 | B1 | 4/2005 | Park |
| 2002/0169485 | A1 * | 11/2002 | Pless et al. ............ 607/48 |
| 2005/0043652 | A1 | 2/2005 | Lovett et al. |
| 2005/0061320 | A1 | 3/2005 | Lee et al. |
| 2005/0101833 | A1 | 5/2005 | Hsu et al. |
| 2005/0148897 | A1 | 7/2005 | Cho et al. |
| 2005/0215847 | A1 | 9/2005 | Heruth et al. |
| 2006/0079802 | A1 | 4/2006 | Jensen et al. |
| 2006/0094972 | A1 | 5/2006 | Drew |

OTHER PUBLICATIONS

Gotman, J. "Automatic Seizure Detection: Improvements and Evaluation", Electroencephalography and Clinical Neurophysiology 76(4): 317-324, (1990).

* cited by examiner

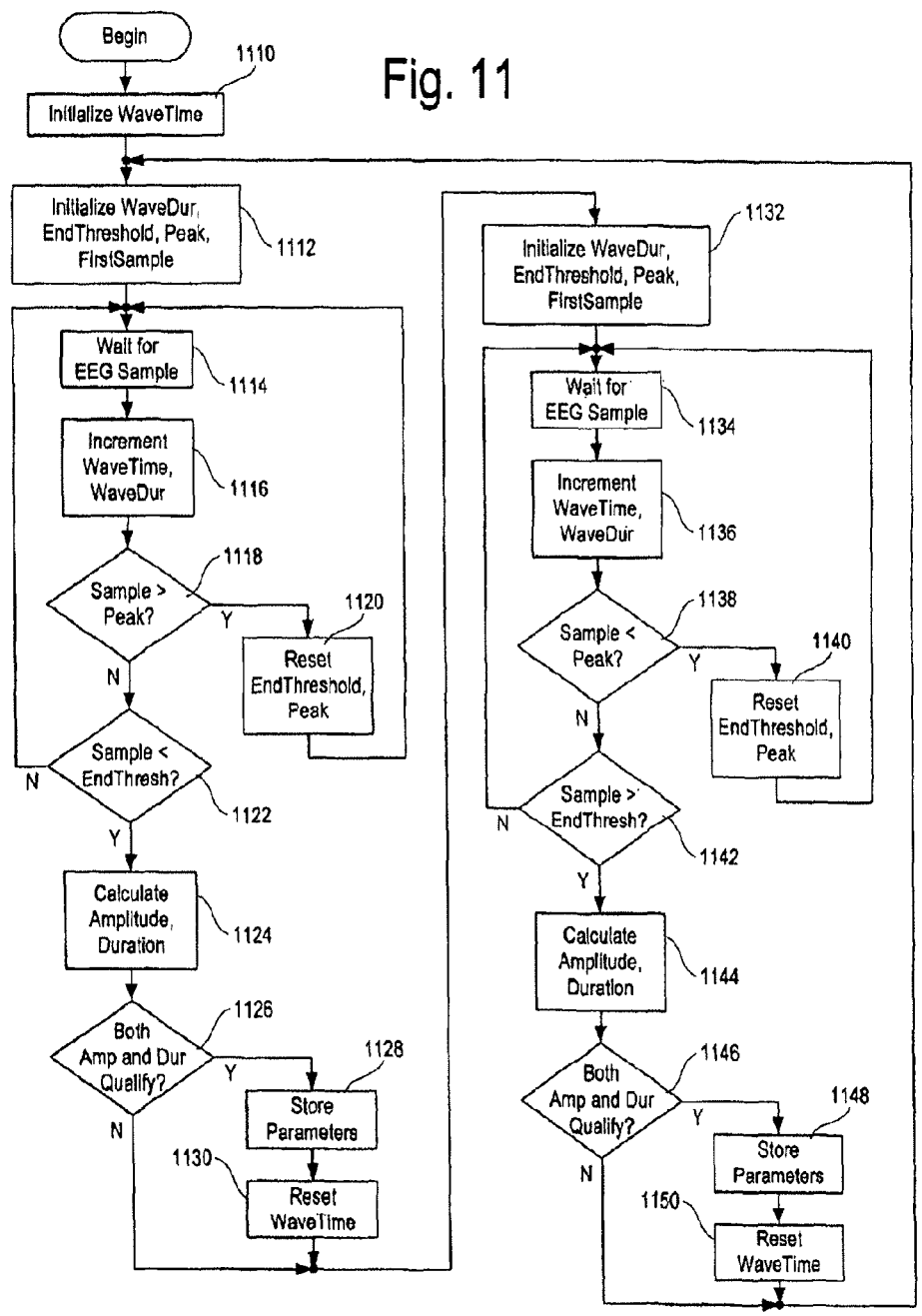

DEVICES AND METHODS FOR MONITORING PHYSIOLOGICAL INFORMATION RELATING TO SLEEP WITH AN IMPLANTABLE DEVICE

CROSS-REFERENCE TO RELATED APPLICATIONS

This application is a continuation application of and claims the benefit of U.S. patent application Ser. No. 13/733,055 filed Jan. 2, 2013 entitled "Devices and Methods for Monitoring Physiological Information Relating to Sleep with an Implantable Device", by Sun et al., and assigned to the assignee of the present application, now U.S. Pat. No. 8,538,514, which is a continuation application of and claims the benefit of U.S. patent application Ser. No. 13/274,037 filed Oct. 14, 2011 entitled "Devices and Methods for Monitoring Physiological Information Relating to Sleep with an Implantable Device", by Sun et al., and assigned to the assignee of the present application, now U.S. Pat. No. 8,369,940, which is a continuation application of and claims the benefit of U.S. patent application Ser. No. 12/971,455, filed Dec. 17, 2010 entitled "Devices and Methods for Monitoring Physiological Information Relating to Sleep with an Implantable Device", by Sun et al., and assigned to the assignee of the present application, now U.S. Pat. No. 8,068,904, which is a divisional application of and claims the benefit of U.S. patent application Ser. No. 11/704,451, filed Feb. 9, 2007 entitled "Devices and Methods for Monitoring Physiological Information Relating to Sleep with an Implantable Device", by Sun et al., and assigned to the assignee of the present application, now U.S. Pat. No. 7,894,890. Each of U.S. Ser. Nos. 13/733,055; 13/274,037; 12/971,455 and Ser. No. 11/704,451 are incorporated by reference herein in the entirety.

BACKGROUND

1. Field

The implantable devices and methods described here relate to the field of sleep staging and sleep monitoring. More specifically, the implantable devices and methods relate to sleep staging and sleep monitoring that is accomplished by detecting and analyzing physiological signals.

2. Background

Sleep is a state of brain activity defined as unconsciousness from which a person can be aroused by sensory or other stimuli (Arthur C. Guyton, *Textbook of Medical Physiology* 659 (8$^{th}$ ed. 1991)). While asleep, a person typically goes through two alternating states of sleep, rapid eye movement (REM) sleep and non-REM sleep. Non-REM sleep is comprised of four sleep stages. Stage 1 (S1) is a state of drowsiness or transition between wake and sleep. Stage 2 (S2) is a state of light sleep. Stage 3 (S3) and stage 4 (S4) are stages of deep sleep. REM sleep occurs about 80 to 100 minutes after falling asleep, and is characterized by high frequency EEG activity, bursts of rapid eye movement, and heightened autonomic activity. Sleep progresses in a cycle from stage 1 through stage 4 to REM sleep. A person typically experiences four to six REM periods per sleep period.

Sleep disorders such as sleep apnea, restless legs syndrome, and narcolepsy, inevitably result in sleep deprivation, which among other things, interferes with work, driving, and social activities. Various neurological and psychiatric conditions are also associated with disruptions of normal sleep patterns. For example, insomnia or oversleeping may occur in individuals with depression, and those experiencing a manic upswing characteristic of bipolar disorder may not sleep at all. Furthermore, because REM sleep increases sympathetic nervous system activity, myocardial ischemia or arrhythmia may be triggered during REM sleep in individuals with pre-existing heart pathology. Thus, the detection and characterization of sleep states is important in the evaluation and treatment of many medical conditions.

Currently, information about sleep stages is obtained using polysomnography, a procedure in which data is acquired related to various body activities, including EEG waveforms, cardiac muscle activity, and breathing. This type of evaluation usually is conducted in a sleep laboratory over one or more nights, and thus is not convenient when it is desirable to monitor a patient over an extended period of time. There are ambulatory sleep monitoring systems, however continuous and extended sleep monitoring can nonetheless be inconvenient because these systems must be applied to the patient and adjusted prior to every sleep episode. Furthermore, many known devices and systems for assessing EEG waveforms (e.g., using time-domain and frequency-domain analysis) require more computational ability than can be easily included in an implantable device.

Accordingly, it would be desirable to have an implantable device capable of continuously monitoring sleep. It would also be desirable to have implantable devices that are capable of detecting different stages of sleep. Similarly, it would be desirable to have implantable devices with monitoring and detecting functions for evaluating and treating various medical conditions associated with disturbed sleep patterns.

SUMMARY

Described here are implantable devices and methods for monitoring sleep and detecting various sleep stages. To detect at least one sleep stage, the implantable devices generally include at least one sensor designed to sense physiological information, a processor configured to process the physiological information using low computational power, and a battery that may or may not be rechargeable. The implantable devices are also capable of processing the physiological information to indicate the quality of sleep, and characterize the information in a manner that helps to diagnose various medical conditions and/or to guide therapy. In some variations, the implantable device is configured to deliver one or more therapies. For example, the implantable device may contain a drug pump or drug-eluting electrode, or may be configured to deliver electrical stimulation.

The implantable device may also include memory that is configured to store at least a portion of the physiological information or the processed physiological information. Additionally, the implantable device may employ a wireless system for transmitting at least a portion of the physiological information or processed physiological information to a remote location.

The type of sensor(s) that are included in the implantable device will depend upon the type of physiological information that it is desired to sense and process. For example, cardiac sensors may be used to obtain cardiac information; neurological sensors may be used to obtain neurological information, positional sensors may used to obtain positional information, and respiratory sensors may be used to obtain respiratory information. More specifically, the types of physiological information that may be sensed include, but are not limited to, heart rate, blood-oxygen saturation, partial pressure of oxygen within the blood, core temperature, head movement, cerebral metabolic rate, and cerebral blood flow. In some instances, the physiological information obtained is electrographic in form. For example, the physiological information may be recorded as an electroencephalogram (EEG), electrocorticogram (ECoG), electrocardiogram (EKG), electromyogram (EMG), or electro-oculogram (EOG).

In one variation, the implantable device may contain at least one sensor, and in other variations, it may include two or more sensors. When two or more sensors are present, they may sense the same or different types of physiological information. The sensor may be either a depth electrode or strip electrode, depending on the nature of the physiological information to be sensed. Examples of strip electrodes include, but are not limited to, electrodes that are placed within or beneath the scalp or on the skull, or electrodes that are epidurally or subdurally placed. Similarly, the depth or strip electrodes may employ monopolar or bipolar sensing. In some variations, the implantable device further includes a stimulation electrode or at least one sensor that is configured to provide stimulation as well as sensing. In other variations, the implantable device further includes a component that is capable of patient-triggered event recording. This component may be a sensor that is designed to sense magnetic field changes.

Methods for detecting sleep stages are also described. In one variation, the method includes sensing physiological information and processing that information using low computational power to detect at least one sleep stage. The REM state, the stages S1, S2, S3, S4, or any combination of the REM state and the sleep stages may be detected. The algorithm may employ half-waves, a histogram counter, a threshold detector, Fourier transforms, or a combination thereof to process the physiological information using low computational power.

The information obtained related to sleep states and stages may be used to diagnose or treat a medical condition, or to guide therapy for a medical condition. Examples of medical conditions include neurological conditions, psychological conditions, cardiac conditions, respiratory conditions, and sleep conditions. In one variation, stimulation is used to treat a medical condition. The stimulation may be selected and regulated based on the sleep state or stage that is detected. Specifically, the stimulation may be regulated by changing the frequency, pulse-width, amplitude, or duration of the stimulation, or by changing the stimulation montage. The stimulation may also be initiated or terminated based on the detection of a particular sleep state or stage.

In another variation, the medical condition is treated by delivery of a drug. The type of drug delivered, dosage, and/or rate of delivery may be based on the particular sleep state or stage detected. Similarly, when drug delivery is initiated or terminated or how drug delivery is regulated may be determined based upon the sleep state or stage a person is experiencing.

BRIEF DESCRIPTION OF THE DRAWINGS

FIG. 9B is a graph of a slow delta wave. FIG. 9C is a graph of a theta wave. FIG. 9D is a graph of an alpha wave.

FIG. 11 is a flow chart of a method of extracting half waves from an EEG signal.

DETAILED DESCRIPTION

Described here are implantable devices and methods for monitoring physiological information relating to sleep for detecting sleep states or stages. The devices may be implanted in or on or adjacent to suitable tissue of any body region. The physiological information may be used to monitor the sleep of a patient, and/or used to diagnose or guide therapy of a medical condition.

The devices are configured to use low computational power to perform device functions. For example, the devices may use customized digital electronics modules that require low power and are minimally reliant upon a central processing unit to implement algorithms to reduce or extract features from data. One advantage of using algorithms that require low computational power is that the actual power consumed by the devices is less than what it would be if a greater degree of computational power was required for the device to carry out its intended functions. Preserving power in an implantable device is especially desirable when the power source for the device, such as a battery, is implanted as well. That is, it is generally desirable for the power supply to be sufficient to carry out the device functions for as long a period of time as possible, to avoid removing or explanting the device to replace it or recharge it. Removing an implantable device can also cause damage to the device leads or other functional or structural features of the device and, of course, explanting or removing any implantable device poses the risk of complications from the surgery which it would be desirable to avoid whenever possible.

Devices for Detecting Sleep Stages

The implantable devices for monitoring physiological information relating to sleep are configured to identify any sleep state, i.e., REM or non-REM, and any of the four standard sleep stages S1, S2, S3, and S4, or any combination of sleep states and stages. In one variation, the implantable device includes at least one sensor that senses physiological information, a processor that processes the physiological information using low computational power to detect at least one sleep state or stage, and a battery. The sensor(s) may be included in a detection subsystem that may also contain a waveform analyzer. The waveform analyzer may be capable of analyzing waveform features (such as half wave characteristics) as well as window-based analyses (such as line length and area under the curve) to provide sleep stage detection. A central processing unit is typically included to consolidate the data received from one or more sensors and coordinate action in reaction or response to the data received when necessary.

Figure 1:
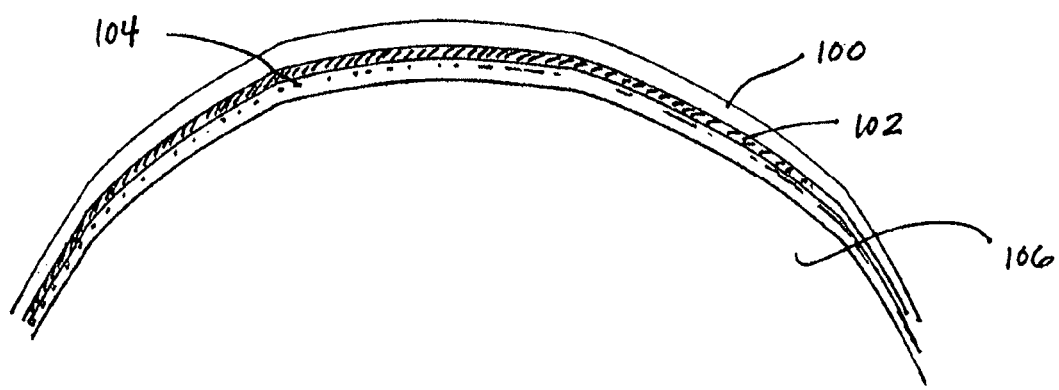
FIG. 1 is a side view of a portion of a person's head where locations are identified at which an implantable device for monitoring physiological information relating to sleep may be implanted.
Figure 2:
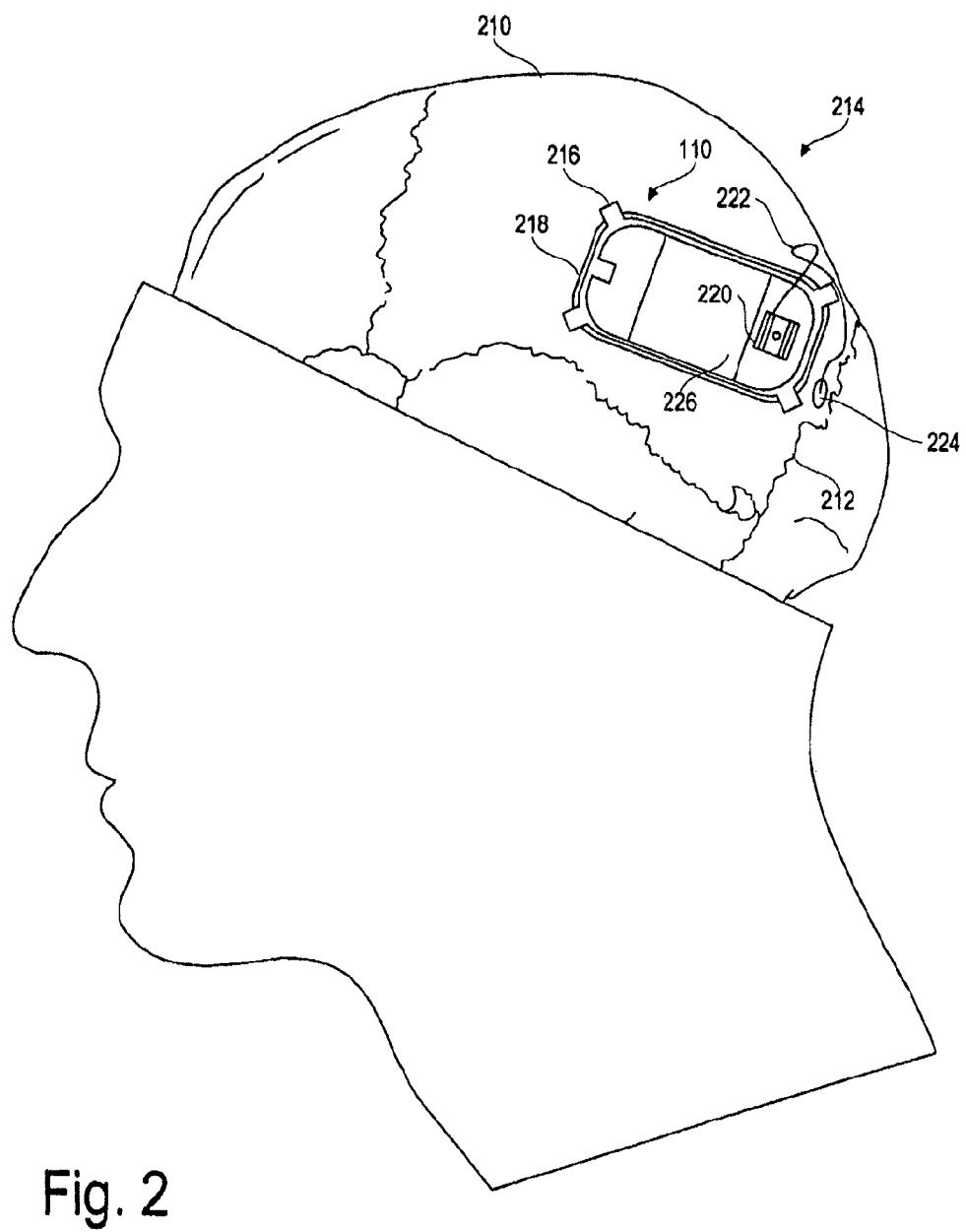
FIG. 2 is a perspective view of an implantable device for monitoring physiological information relating to sleep within the cranium.

One variation of an implantable device is illustrated in FIG. 2. In FIG. 2, the implantable device 110 is shown within one of the parietal bones 210 of the skull of a patient, in a location anterior to the lambdoidal suture 212. It should be noted, however, that the placement described and illustrated herein is merely exemplary, and other locations and configurations are also possible, in the cranium or elsewhere, depending on the size and shape of the device and individual patient needs, among other factors. The device 110 may be configured to fit the contours of the patient's cranium 214. In another variation (shown in FIG. 1), the device may be implanted within or under the scalp 100, within or under the skull 102, under the dura mater 104, or within the brain 106. In yet another variation, the device may be implanted within the chest wall, e.g., within the pectoral region (not shown), with leads extending through the patient's neck and between the patient's cranium and scalp, as necessary.

Referring to FIG. 2, the implantable device 110 may be placed within the patient's cranium 214 by way of a ferrule 216. The ferrule 216 is a structural member adapted to fit into a cranial opening, attach to the cranium 214, and retain the device 110. To implant the device 110, a craniotomy is performed in the parietal bone anterior to the lambdoidal suture 212 to define an opening 218 slightly larger than the device 110. The ferrule 216 is inserted into the opening 218 and affixed to the cranium 214, as with bone screws ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates the electrical connection between a conductor in the lead 222 and circuitry within the device 110. The lead connector 220 accomplishes this in a substantially fluid-tight environment with biocompatible materials.

The lead 222 is a flexible elongated member having one or more conductors. The lead 222 is coupled to the device 110 via the lead connector 220, and is generally situated on the outer surface of the cranium 214 (and under the patient's scalp 100), extending between the device 110 and a burr hole 224 or other cranial opening, where the lead 222 enters the cranium 214 and is coupled to an electrode implanted in a desired location in the patient's brain. As described in U.S. Pat. No. 6,006,124 to Fischell, et al., which is hereby incorporated by reference in its entirety, the burr hole 224 may be wholly or partially sealed, e.g., with a burr hole cover, after implantation to prevent further movement of the lead 222.

The device 110 may include a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other desirable features. As will be described in further detail below, a telemetry coil may be provided outside of the housing 226 (and potentially integrated with the lead connector 220) to facilitate communication between the device 110 and external devices. The battery included in the implantable devices may be rechargeable. In general, the implantable devices may generally have a long-term average current consumption on the order of 10 microamps, which allows them to operate on power provided by a coin cell or similarly small battery for a period of years without need for battery replacement. It should be noted, however, that as battery and power supply configurations vary, the long-term average current consumption of a device may also vary and still provide satisfactory performance.

The configuration of the implantable device 110 provides several advantages over known alternative designs. First, the self-contained nature of the device substantially decreases the need for access to the device 110, allowing the patient to participate in normal life activities. Its small size and intracranial placement also may cause minimal cosmetic disfigurement. The device 110 will typically fit in an opening in the patient's cranium, under the patient's scalp, with little noticeable protrusion or bulge. Furthermore, the ferrule 216 used for implantation allows a craniotomy to be performed and fit verified before the device 110 is implanted, thus avoiding the risk of breaking the device during this fitting process. The ferrule 216 also protects the brain from the device in the event the brain is subjected to significant external pressure or impact by providing a structural support for the device in the skull. A further advantage is that the ferrule 216 receives any cranial bone growth, so when the device is explanted or removed, any cranial bone that has grown since the time of implant will impinge upon the ferrule, not the device, so that the device can be taken out and/or replaced with another device without the need to remove any bone screws that are used to secure the ferrule 216. Only the fasteners that are used to retain the device 110 in the ferrule 216 need be manipulated.

Figure 3:
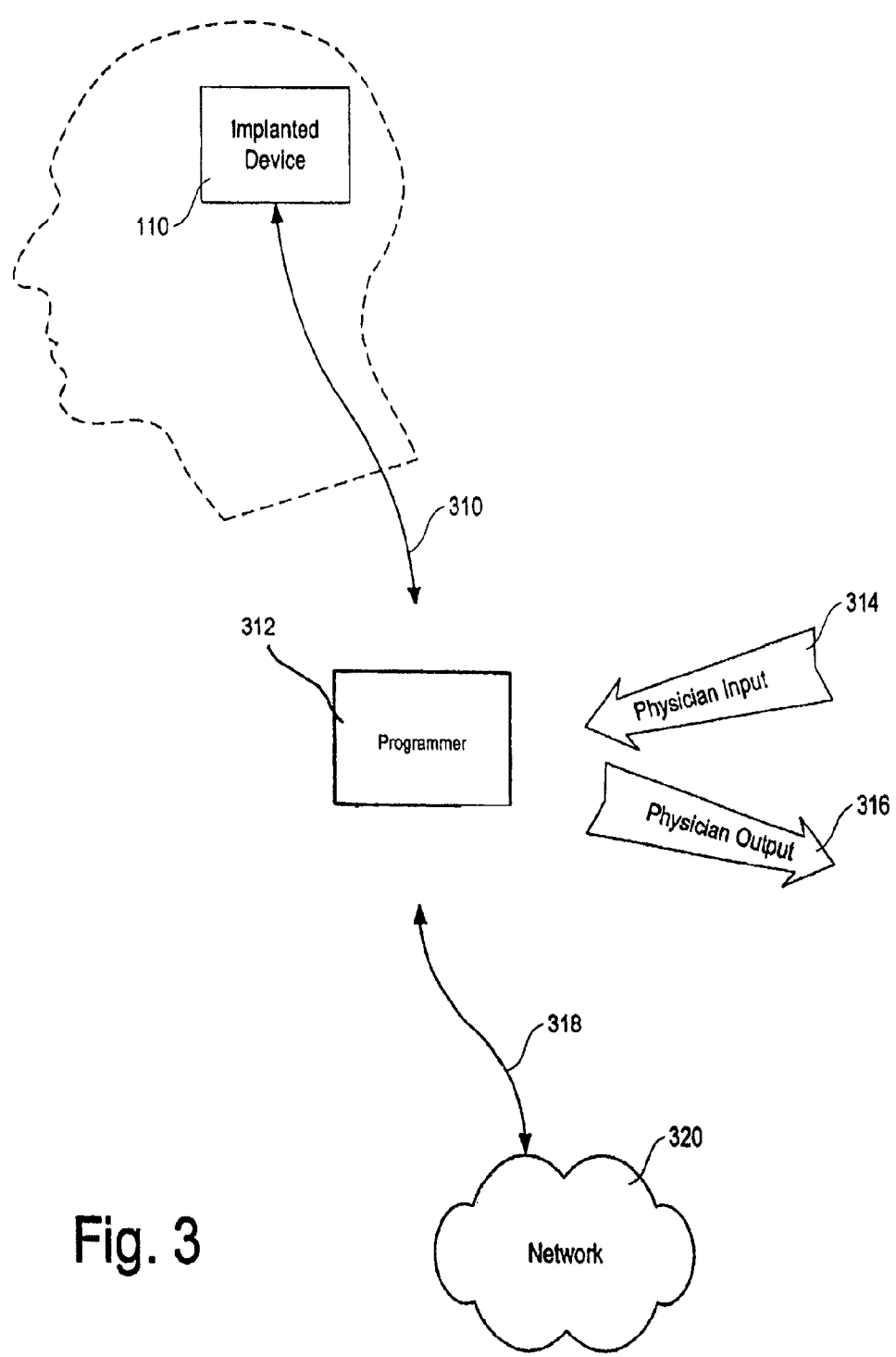
FIG. 3 is a schematic diagram of a method for monitoring physiological information relating to sleep.

As stated above, and as illustrated in FIG. 3, the implantable device may operate in conjunction with external equipment. The device 110 is mostly autonomous (particularly when performing its usual sensing, detection, and stimulation capabilities), but may include a wireless link 310 that can be selectively engaged to external equipment such as a programmer 312 (e.g., a handheld programmer). The wireless link 310 may be established by moving a wand or other suitable apparatus into range of the device 110 where the wand or other apparatus has wireless communication capabilities and is coupled to the programmer 312. The programmer 312 can then be used to manually control the operation of the device 110, as well as to transmit information to, or receive information from, the device 110. Several specific capabilities and operations the programmer 312 can perform in conjunction with the device 110 are described in further detail below.

The programmer 312 is capable of performing a number of operations. In particular, the programmer 312 may be able to specify and set variable parameters in the device 110 to adapt the function of the device 110 to meet the patient's needs, download or receive data (including but not limited to stored electrographic waveforms, detections, parameters, or logs of actions taken) from the device 110 to the programmer 312, upload or transmit program code and other information from the programmer 312 to the device 110, or command the device 110 to perform specific actions or change modes as desired by a physician operating the programmer 312. To facilitate these functions, the programmer 312 is adapted to receive physician input 314 and provide physician output 316. The data may be transmitted between the programmer 312 and the device 110 over the wireless link 310.

The programmer 312 may be coupled via a communication link 318 to a network 320 such as the Internet. This allows any information downloaded from the device 110, as well as any program code or other information to be uploaded to the device 110, to be stored in a database at one or more data repository locations (which may include various servers and network-connected programmers like the programmer 312). Patients and/or physicians can thereby have access to important data, including past monitoring results and/or information concerning treatment of medical conditions and the results of treatment, and software updates, essentially anywhere in the world where there is a programmer (like the programmer 312) and a network connection.

Figure 4:
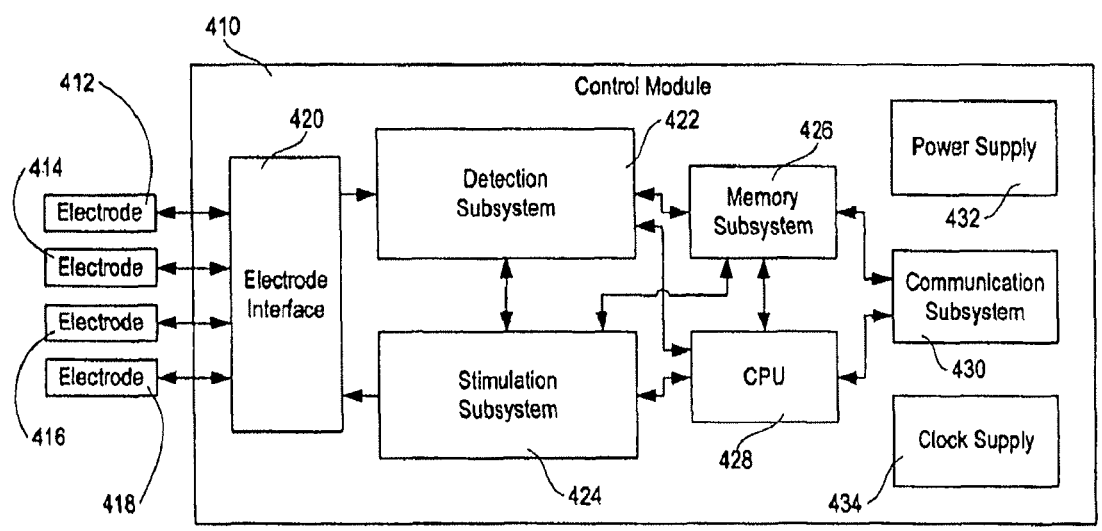
FIG. 4 is a block diagram of an implantable device for monitoring physiological information relating to sleep.

A block diagram of an implantable device 110 for monitoring physiological information relating to sleep is illustrated in FIG. 4. Inside the housing 226 (shown in FIG. 2) of the device 110 there are several subsystems making up a control module 410. The control module 410 is capable of being coupled to a plurality of electrodes 412, 414, 416, and 418 (each of which may be connected to the control module 410 via a lead that is analogous or identical to the lead 222 of FIG. 2) for sensing physiological information and providing stimulation, when desired. The coupling may be accomplished through the lead connector 220 (FIG. 2). Although four electrodes are shown in FIG. 4, it should be recognized that any number of electrodes is possible. For example, it is possible to employ a single lead with at least two electrodes, or two leads each with a single electrode (or with a second electrode provided by a conductive exterior portion of the housing 226).

The electrodes 412, 414, 416, and 418 are connected to an electrode interface 420. The electrode interface is capable of selecting each electrode as required for sensing and/or stimulation. Accordingly, the electrode interface 420 is coupled to a detection subsystem 422 and/or a stimulation subsystem 424. When the electrodes 412, 414, 416, and 418 are designed primarily for sensing physiological information, a stimulation subsystem 424 will typically not be included in the control module 410. The electrode interface 420 also may provide any other features, capabilities, or aspects, including but not limited to, amplification, isolation, and charge-balancing functions, that are required for a proper interface with, e.g., neurological tissue, and not provided by any other subsystem of the device 110.

The detection subsystem 422 may include an EEG (and/or ECoG) analyzer function. The EEG analyzer function may be adapted to receive EEG signals from the electrodes 412, 414, 416, and 418 through the electrode interface 420, and process those EEG signals to identify neurological activity indicative of various sleep states or stages. One way to implement such EEG analysis functionality is disclosed in detail in U.S. Pat. No. 6,016,449 to Fischell et al., incorporated by reference above. In another variation, the detection subsystem may include a set of sensors built specifically for sensing low-frequency EEG and/or ECoG signals associated with sleep. These sensors may be configured as a set of half-wave detectors with allowable minimum and maximum amplitude ranges and window durations to sense signals within the delta (0.5-3.5 Hz), theta (4-7.5 Hz), and alpha (8-12 Hz) bands. Depending on the particular indication of use, however, the sleep sensors may be adjusted to sense other frequency bands. The detections may be made using bipolar or monopolar recording. While monopolar recording is desirable since sleep patterns are often synchronous over large cortical regions, adjusting the recording montage appropriately may be necessary to optimize bipolar recordings for sleep monitoring. The detection subsystem may optionally also contain further sensing and detection capabilities, including but not limited to parameters derived from other physiological information (such as electrophysiological parameters, temperature, blood pressure, heart rate, position (including head position), movement, etc.).

The detection subsystem may use the preexisting electrodes that were placed for neurostimulation for sleep state or stage detection, or additional electrodes may be placed for optimum detection. For example, if noncortical leads were implanted for neurostimulation, an additional lead may be placed over the occipital cortex, or other desired cortex location, for sleep monitoring. Cardiac sensors (cardiac electrodes) may also be used to sense electrical activity (e.g., heart rate and conduction) of the heart. Respiratory sensors may be included that are configured to sense various respiratory parameters, such as respiratory rate, tidal volume, and minute ventilation.

The sensors may be coupled to a low-speed, low-power central processing unit that detects and processes the sensor data. For example, the central processing unit may be configured to have a processing speed of between about 100 Hz to about 1000 Hz. In some cases, a processing speed of less than 100 Hz may be utilized. A processor may be included to receive EEG and/or ECoG data from the sensors. The processor may perform sleep state or stage detection on a real-time basis, or may process previously acquired and stored sensor data in a batch mode to retrospectively classify sleep stages of one or more sleep periods. The central processing unit may remain in a suspended "quiet" state characterized by relative inactivity for a substantial percentage of the time, and then may be periodically awakened by interruptions from the detection subsystem to perform certain tasks related to the detection and prediction schemes enabled by the device.

If included, the stimulation subsystem 424 is capable of applying electrical stimulation to tissue through the electrodes 412, 414, 416, and 418. This can be accomplished in any of a number of different ways. For example, it may be advantageous in some circumstances to provide stimulation in the form of a substantially continuous stream of pulses or, alternatively, on a scheduled basis. In some instances, therapeutic stimulation may be provided in response to specific sleep stages detected by the EEG analyzer function of the detection subsystem 422. As illustrated in FIG. 4, the stimulation subsystem 424 and the EEG analyzer function of the detection subsystem are in communication with each other. This facilitates the ability of stimulation subsystem 424 to provide responsive stimulation as well as an ability of the detection subsystem 422 to blank the amplifiers while stimulation is being performed to minimize stimulation artifacts. It is contemplated that the parameters of the stimulation signal (e.g., frequency, duration, waveform) provided by the stimulation subsystem 424 would be specified by other subsystems in the control module 410, as will be described in further detail below.

A memory subsystem 426 and a central processing unit (CPU) 428, which can take the form of a microcontroller, may also be included in the control module 410. The memory subsystem is coupled to the detection subsystem 422 (e.g., for receiving and storing data representative of sensed EEG signals and evoked responses), the stimulation subsystem 424 (e.g., for providing stimulation waveform parameters to the stimulation subsystem), and the CPU 428, which can control the operation of the memory subsystem 426. In addition to the memory subsystem 426, the CPU 428 may also be connected to the detection subsystem 422 and the stimulation subsystem 424 for direct control of those subsystems.

Also provided in the control module 410, and coupled to the memory subsystem 426 and the CPU 428, is a communication subsystem 430. The communication subsystem 430 enables communication between the device 110 and the outside world, particularly the external programmer 312 (FIG. 3). As set forth above, the communication subsystem 430 may include a telemetry coil (which may be situated outside of the housing 226), which enables transmission and reception of signals, to or from an external apparatus via inductive coupling. Alternatively, the communication subsystem 430 may use an antenna for an RF link or an audio transducer for an audio link.

Further subsystems in the control module 410 are a power supply 432 and a clock supply 434. The power supply 432 supplies the voltages and currents necessary for each of the other subsystems. The clock supply 434 supplies substantially all of the other subsystems with any clock and timing signals necessary for their operation.

It should be observed that while the memory subsystem 426 is illustrated in FIG. 4 as a separate functional subsystem, the other subsystems may also require various amounts of memory to perform the functions described above and others. Furthermore, while the control module 410 is shown as a single physical unit contained within a single physical enclosure, namely the housing 226 (FIG. 2), it may comprise a plurality of spatially separate units, with each performing a subset of the capabilities described above. Also, it should be noted that the various functions and capabilities of the subsystems described above may be performed by electronic hardware, computer software (or firmware), or a combination thereof. The division of work between the CPU 428 and the other functional subsystems may also vary.

Figure 5:
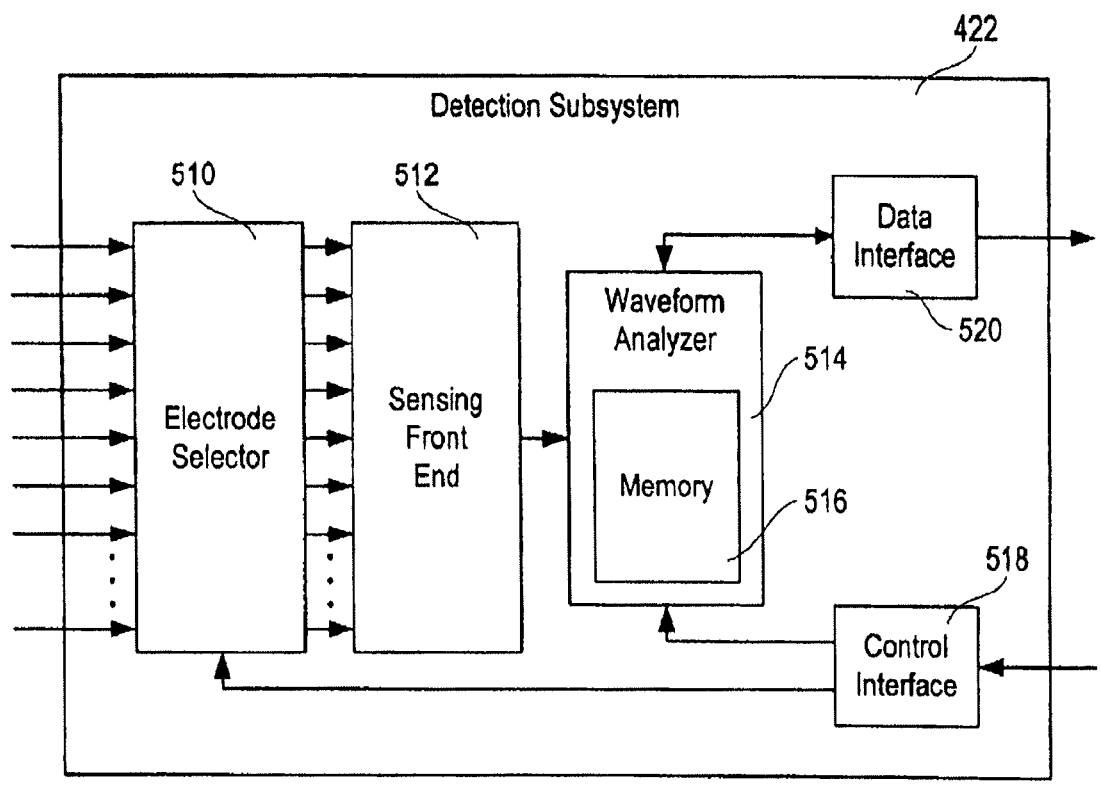
FIG. 5 is a block diagram of a detection subsystem of the implantable device shown in FIG. 4.

The detection subsystem is further detailed in FIG. 5. In FIG. 5, inputs from the electrodes 412, 414, 416, and 418 (FIG. 4) are depicted on the left, and connections to other subsystems are shown on the right. Signals received from the electrodes 412, 414, 416, and 418 (as routed through the electrode interface 420) are received in an electrode selector 510. The electrode selector 510 allows the device to select which electrodes (of the electrodes 412, 414, 416, 418) should be routed to which individual sensing channels of the detection subsystem 422, based on commands received through a control interface 518 from the memory subsystem 426 or the CPU 428 (FIG. 4). In one variation, each sensing channel of the detection subsystem 422 receives a monopolar or bipolar signal representative of the difference in electrical potential between two selectable electrodes. Accordingly, the electrode selector 510 provides signals corresponding to each pair of selected electrodes (of the electrodes 412, 414, 416, 418) to a sensing front end 512, which performs amplification, analog-to-digital conversion, and multiplexing functions on the signals in the sensing channels. The sensing front end will be described further below in connection with FIG. 6. In another variation, each sensing channel of the detection subsystem 422 may receive a monopolar or bipolar signal representative of the difference in electrical potential between an electrode and the housing of the implantable device (which may also serve as an electrode).

A multiplexed input signal representative of all active sensing channels is then fed from the sensing front end 512 to a waveform analyzer 514. The waveform analyzer 514 may include a special-purpose digital signal processor (DSP) or, in another variation, may comprise a programmable general-purpose DSP. Referring to FIG. 5, the waveform analyzer may have its own scratchpad memory area 516 for local storage of data and program variables when signal processing is being performed. In either case, the signal processor performs suitable measurement and detection methods described generally above and in greater detail below. Any results from such methods, as well as any digitized signals intended for storage transmission to external equipment, are passed to various other subsystems of the control module 410, including the memory subsystem 426 and the CPU 428 (FIG. 4), through a data interface 520. Similarly, the control interface 518 allows the waveform analyzer 514 and the electrode selector 510 to be in communication with the CPU 428.

Figure 6:
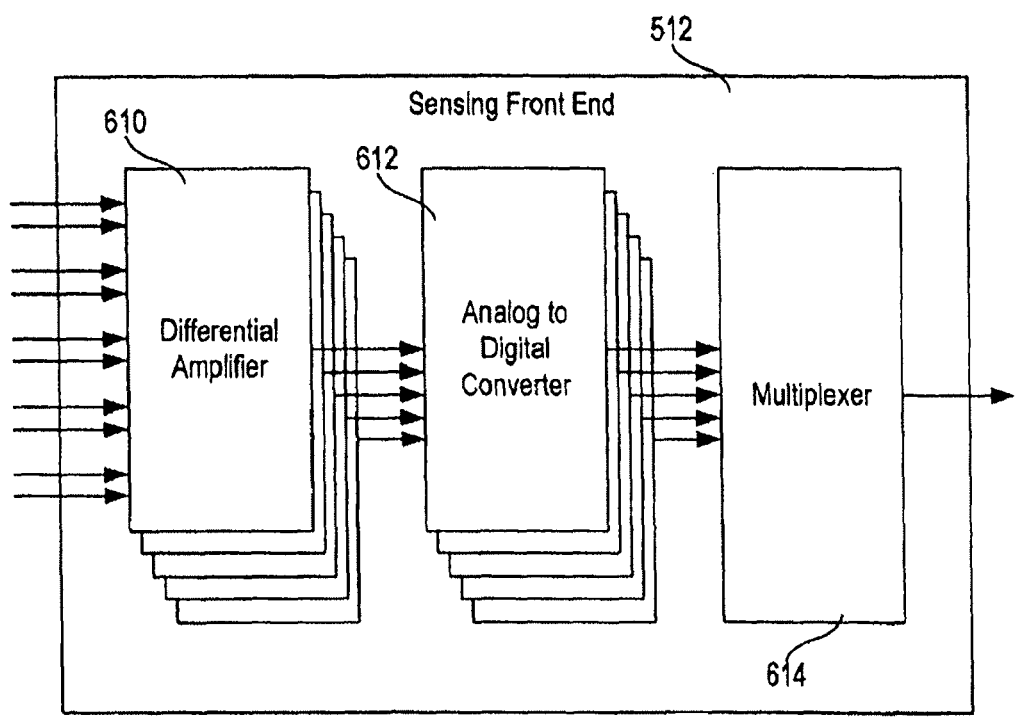
FIG. 6 is a block diagram of a sensing front end of the detection subsystem of FIG. 5.

Referring now to FIG. 6, the sensing front end 512 is illustrated in further detail. As shown, the sensing front end includes a plurality of differential amplifier channels 610, each of which receives a selected pair of inputs from the electrode selector 510 or from the electrode selector 510 and implantable device housing. In one variation, each of the differential amplifier channels 610 is adapted to receive or to share inputs with one or more other differential amplifier channels 610 without adversely affecting the sensing and detection capabilities of the implantable device. In another variation, there are at least eight electrodes, which can be mapped separately to eight differential amplifier channels 610 representing eight different sensing channels and capable of individually processing eight bipolar signals, each of which represents an electrical potential difference between two monopolar input signals received from the electrodes and applied to the sensing channels via the electrode selector 510. For clarity, only five channels are illustrated in FIG. 6, but it should be noted that any practical number of sensing channels may be employed.

Each differential amplifier channel 610 feeds a corresponding analog-to-digital converter (ADC) 612. The analog-to-digital converters 612 may be separately programmable with respect to sample rates. In one variation, the ADCs 612 convert analog signals into 10-bit unsigned integer digital data streams at a sample rate selectable between 250 Hz and 500 Hz. In other variations where waveforms are used, as described below, sample rates of 250 Hz are typically used. However, numerous sample rate and resolution options are possible, with tradeoffs known to individuals of ordinary skill in the art of electronic signal processing. The resulting digital signals are received by a multiplexer 614 that creates a single interleaved digital data stream representative of the data from all active sensing channels. As will be described in further detail below, not all of the sensing channels need to be used at one time, and it may in fact be advantageous in certain circumstances to deactivate certain sensing channels to reduce power consumption.

It should be noted that as illustrated and described herein, a "sensing channel" is not necessarily a single physical or functional item that can be identified in any illustration. Rather, a sensing channel is formed from the functional sequence of operations described herein, and particularly represents a single electrical signal received from any pair or combination of electrodes (including the implantable device housing, which can serve as an electrode), as preprocessed by a method for monitoring physiological information relating to sleep with an implantable device, in both analog and digital forms. See, e.g., U.S. Pat. No. 6,473,639 to D. Fischell et al., filed on Mar. 2, 2000, and entitled "Neurological Event Detection Using Processed Display Channel Based Algorithms and Devices Incorporating These Procedures," which is hereby incorporated by reference in its entirety. At times (particularly after the multiplexer 614), multiple sensing channels are processed by the same physical and functional components of the system; notwithstanding that, it should be recognized that unless the description herein indicates to the contrary, the implantable devices described herein process, handle, and treat each sensing channel independently. Referring again to FIG. 6, the interleaved digital data stream is passed from the multiplexer 614, out of the sensing front end 512, and into the waveform analyzer 514. The waveform analyzer 514 is illustrated in greater detail in FIG. 7.

Figure 7:
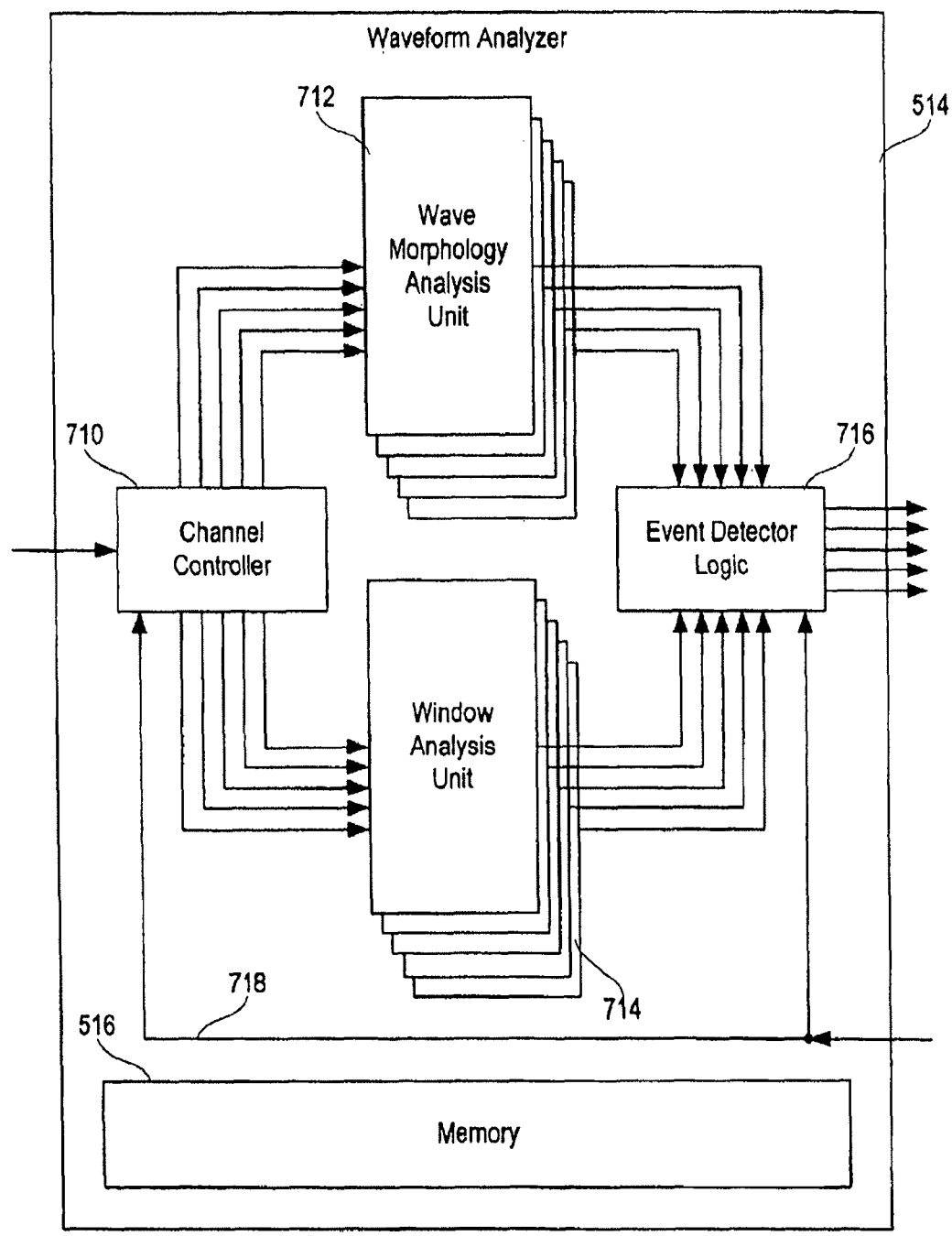
FIG. 7 is a block diagram of a waveform analyzer of the detection subsystem of FIG. 5.

In FIG. 7, the interleaved digital data stream representing information from all of the active sensing channels is first received by a channel controller 710. The channel controller applies information from the active sensing channels to a number of wave morphology analysis units 712 and window analysis units 714. It is preferred to have as many wave morphology analysis units 712 and window analysis units 714 as possible, consistent with the goals of efficiency, size, and low power consumption necessary for an implantable device. In one variation, there are sixteen wave morphology analysis units 712 and eight window analysis units 714, each of which can receive data from any of the sensing channels of the sensing front end 512, and each of which can be operated with different and independent parameters, including differing sample rates, as will be discussed in further detail below.

Each of the wave morphology analysis units 712 operates to extract certain feature information from an input waveform as described below in conjunction with FIGS. 9A-11. Similarly, each of the window analysis units 714 performs certain data reduction and signal analysis within time windows in the manner described in conjunction with FIG. 12-17. Output data from the various wave morphology analysis units 712 and window analysis units 714 may be combined via event detector logic 716. The event detector logic 716 and the channel controller 710 may be controlled by control commands 718 received from the control interface 518 (FIG. 5).

The term "detection channel," as used herein, refers to a data stream including the active sensing front end 512 and the analysis units of the waveform analyzer 514 processing that data stream, in both analog and digital forms. It should be noted that each detection channel can receive data from a single sensing channel and each sensing channel can be applied to the input of any combination of detection channels. The latter selection is accomplished by the channel controller 710. As with the sensing channels, not all detection channels need to be active; certain detection channels can be deactivated to save power or if additional detection processing is deemed unnecessary in certain applications.

In conjunction with the operation of the wave morphology analysis units 712 and the window analysis units 714, a memory area (e.g., scratchpad memory) 516 may be provided for temporary storage of processed data. The memory area 516 may be physically part of the memory subsystem 426, or alternatively may be provided for the exclusive use of the waveform analyzer 514. Other subsystems and components of the implantable device may also be furnished with local memory if such configurations are beneficial.

Figure 8:
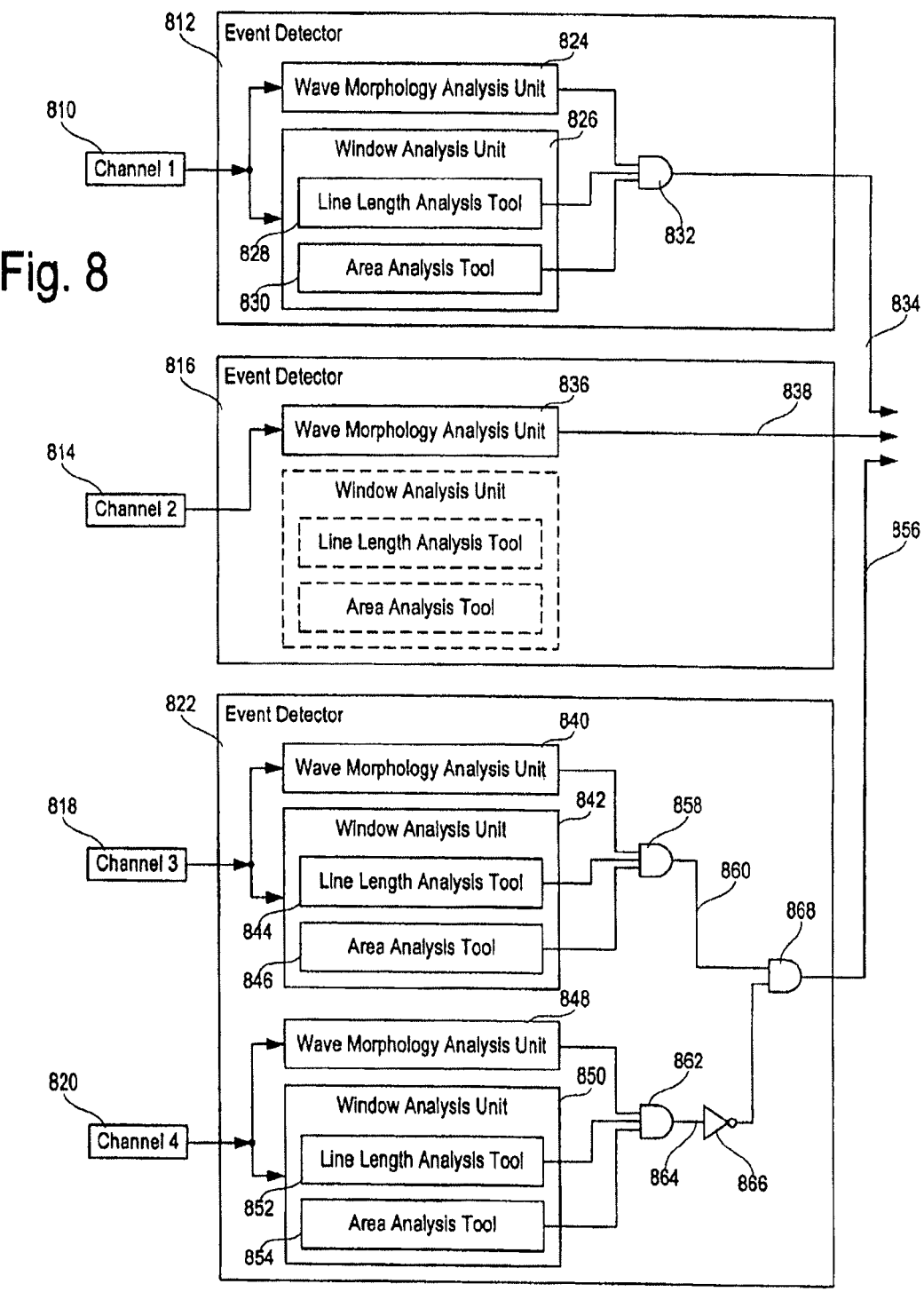
FIG. 8 is a block diagram of certain components of the waveform analyzer of the detection subsystem of FIG. 5.

The operation of the event detector logic 716 (i.e., sleep stage detector logic) is illustrated in detail in the functional block diagram of FIG. 8, which shows four exemplary sensing channels 810, 814, 818, and 820 and three illustrative event detectors 812, 816, and 822 for analyzing the data from the sensing channels. A first sensing channel 810 ("Channel 1" in FIG. 8) provides input to a first event detector 812. (It should be recognized the blocks shown in FIG. 8 denote function, and a particular block may or may not correspond to a physical structure in the implantable device.) A second sensing channel 814 ("Channel 2" in FIG. 8) provides input to a second event detector 816, and a third sensing channel 818 ("Channel 3" in FIG. 8) and a fourth sensing channel 820 ("Channel 4" in FIG. 8) both provide input to a third event detector 822.

The processing that is performed in association with each of the three event detectors 812, 816, and 822 will now be described, again with reference to FIG. 8. The first sensing channel 810 ("Channel 1") feeds a signal to the first event detector 812, which is applied to both a wave morphology analysis unit 824 (e.g., one of the wave morphology analysis units 712 of FIG. 7) and a window analysis unit 826 (e.g., one of the window analysis units 714 of FIG. 7). The window analysis unit 826, in turn, includes a line length analysis tool 828 and an area analysis tool 830. As will be discussed in detail below, the line length analysis tool 828 and the area analysis tool 830 analyze different aspects of the signal from the first input channel 810.

The outputs from the wave morphology analysis unit 824, the line length analysis tool 828, and the area analysis tool 830 of the first event detector 812 are combined in a Boolean "AND" operation 832 into a single output for the first event detector 834. The output 834 then may be used by another system or subsystem for further monitoring or analysis. For example, if a combination of analysis tools in an event detector identifies several simultaneous (or near-simultaneous) types of activity in an input channel, another system or subsystem in the implantable device or operating in conjunction with the implantable device may be programmed to perform an action in response to the output 834. Details of the analysis tools and the combination processes used in the event detectors herein described will be set forth in greater detail below.

In the second event detector 816, which receives input from second sensing channel 814 ("Channel 2"), only a wave morphology analysis unit 836 is active. Accordingly, no Boolean operation needs to be performed, and the wave morphology analysis unit 836 is used directly as an event detector output 838.

The third event detector 822 receives signals from both the third input sensing channel 818 ("Channel 3") and the fourth input sensing channel 820 ("Channel 4"), and includes two separate detection channels of analysis units: a first wave morphology analysis unit 840 and a first window analysis unit 842, the first window analysis unit 842 including a first line length analysis tool 844 and a first area analysis tool 846; and a second wave morphology analysis unit 848 and a second window analysis unit 850, the second window analysis unit 850 including a second line length analysis tool 852 and a second area analysis tool 854. The two detection channels of analysis units in the third event detector 822 are thus processed and operated on so as to provide a single third event detector output 856.

More specifically, the signal from the third sensing channel 818 is input into one of the two wave morphology analysis units (e.g., wave morphology analysis unit 840 in FIG. 8) of the third event detector 822, and the signal from the fourth sensing channel 820 is input into the other of the two wave morphology analysis units (e.g., wave morphology analysis unit 848 in FIG. 8). Each of the inputs from the third sensing channel 818 and the fourth sensing channel 820 is also introduced into a window analysis unit (e.g., the signal from the third sensing channel 818 is input into window analysis unit 842 in FIG. 8 as well as into wave morphology analysis unit 840, and the signal from the fourth sensing channel 820 is input into window analysis unit 850 as well as into wave morphology unit 848. Each of the two window analysis units 842 and 850 of the third event detector 822 have a line length analysis tool (844 and 852) and an area analysis tool (846 and 854). Thus, there are three analysis unit outputs associated with one of the two channels in the third event detector 822 (e.g., third sensing channel 818) and the same three types of analysis unit outputs associated with the other of the two channels in the third event detector 822 (e.g., fourth sensing channel 820). The three analysis unit outputs associated with each channel 818, 820 can be combined via a Boolean "AND" operation 858, 862 to produce two different outputs of a first stage of the third event detector, 860 and 864, respectively. These two outputs 860 and 864 can be combined in a second Boolean "AND" operation 868 into a second stage to produce the final output for the third event detector 856.

Depending upon the nature of the signals being sensed and any processing that is applied to the sensed signals in the event detectors, it may be desirable to invert one or more outputs before or after the outputs are combined in a Boolean "AND" operation. For example, with reference to the third event detector 822, the one of the two outputs of the first stage of the third event detector, i.e., the output 864 in FIG. 8 is shown being inverted in FIG. 8 (as represented in the figure by the "NOT" gate or inverter symbol 866), before the output 864 is further combined in a Boolean "AND" operation with the other output of the first stage of the third event detector, i.e., output 860 in FIG. 8, to produce a second-stage third event detector output 856.

In one variation of an event detector such as the third event detector 822 shown in FIG. 8, the event detector can be configured to monitor or detect a "qualifying event," such as the occurrence of the REM sleep state. More particularly, the processing of, and logical operations applied to, the data input to the third sensing channel 818 and the fourth sensing channel 820 may be such that the second-stage output of the third event detector, i.e., output 856, only is "on" (or "high" or a "1" value as opposed to a "0" value) when a patient is in the REM sleep state. For example, the input received by the third sensing channel 818 may correspond to an EEG signal from the left hemisphere of a patient's brain, and the input received by the fourth sensing channel 820 may correspond to an EEG signal from the right hemisphere of the patient's brain. When both sensing channels 818 and 820 are sensing an EEG signal with characteristics indicative of the REM sleep state, the third event detector 822 can be configured so that the output of the second stage of the third event detector (output 856) will be on (or "high" or a "1" value) for so long as the two EEG signals are indicative of REM sleep. In addition, the both first stage outputs of the third event detector (860 and 864) can be independently configured for selectable persistence (i.e., the ability to retain a value indicating the presence of REM sleep some time after the REM sleep state is actually sensed by the third sensing channel 818 and the fourth sensing channel 820. Thus, the system can be configured so that the combination of the two outputs of the first-stage of the third event detector, namely, outputs 860 and 864, specifically the second-stage output of the third event detector 856 (shown in FIG. 8 as the result of the Boolean "AND" operation illustrated by "AND" gate 868), will remain triggered even when there is not precise temporal synchronization between detections on the sensing channels.

The EEG signals may be introduced to the sensing channels by amplifying signals detected by electrodes capable of sensing electrical activity in the brain. It will be apparent that the location of the electrodes may be other than in the right and left hemispheres, and that the signals received by the sensing channels may be other than EEG signals. Moreover, it will be apparent that the same use of the event detectors of the implantable device, such as the third event detector 822 of FIG. 8, can be used to configure one or more "qualifying channels" for different types of signals, and that the output that represents that a qualifying event is occurring or has occurred may reflect use of something other than a Boolean "AND" operation (e.g., a Boolean "OR" operation) to identify that the event is occurring or has occurred.

In one variation, the "qualifying channel" is applied to detect when noise is occurring on a channel in excess of a certain threshold, so that the output of the second stage of the third event detector output 856 is only "on" when the noise is below that threshold. In another variation, the "qualifying channel" is applied to aid in configuring the implantable device 110, for example, to help determine which of two sets of detection parameters is preferable (by configuring two sensing channels of an event detector to receive signals each corresponding to a different set of parameters on each of two sensing channels of an event detector, and then using a Boolean "OR" operation to indicate when which set of parameters is present on which channel. In still another variation, the sensing channels, processing of and logical operations on the signals can be configured so that a specific temporal sequence of detections must be occurring or have occurred in order for the ultimate output of the event detector to be "on." There are numerous other possibilities for signal processing and logical operations for the event detectors of the implantable device 110. For example, a first event detector output 834, a second event detector output 838 and a third event detector output 856 may be represented by Boolean flags and, as described below, provide information useful for the operation of the implantable devices 110.

While FIG. 8 illustrates four different sensing channels providing input to three event detectors, it should be noted that in a maximally flexible variation, each sensing channel would be allowed to connect to one or more event detectors. It may be advantageous to program (using hardware, firmware, software, or some combination thereof) the different event detectors with different settings (e.g., thresholds) to facilitate alternate "views" of the same sensing channel data stream.

Figure 9A:
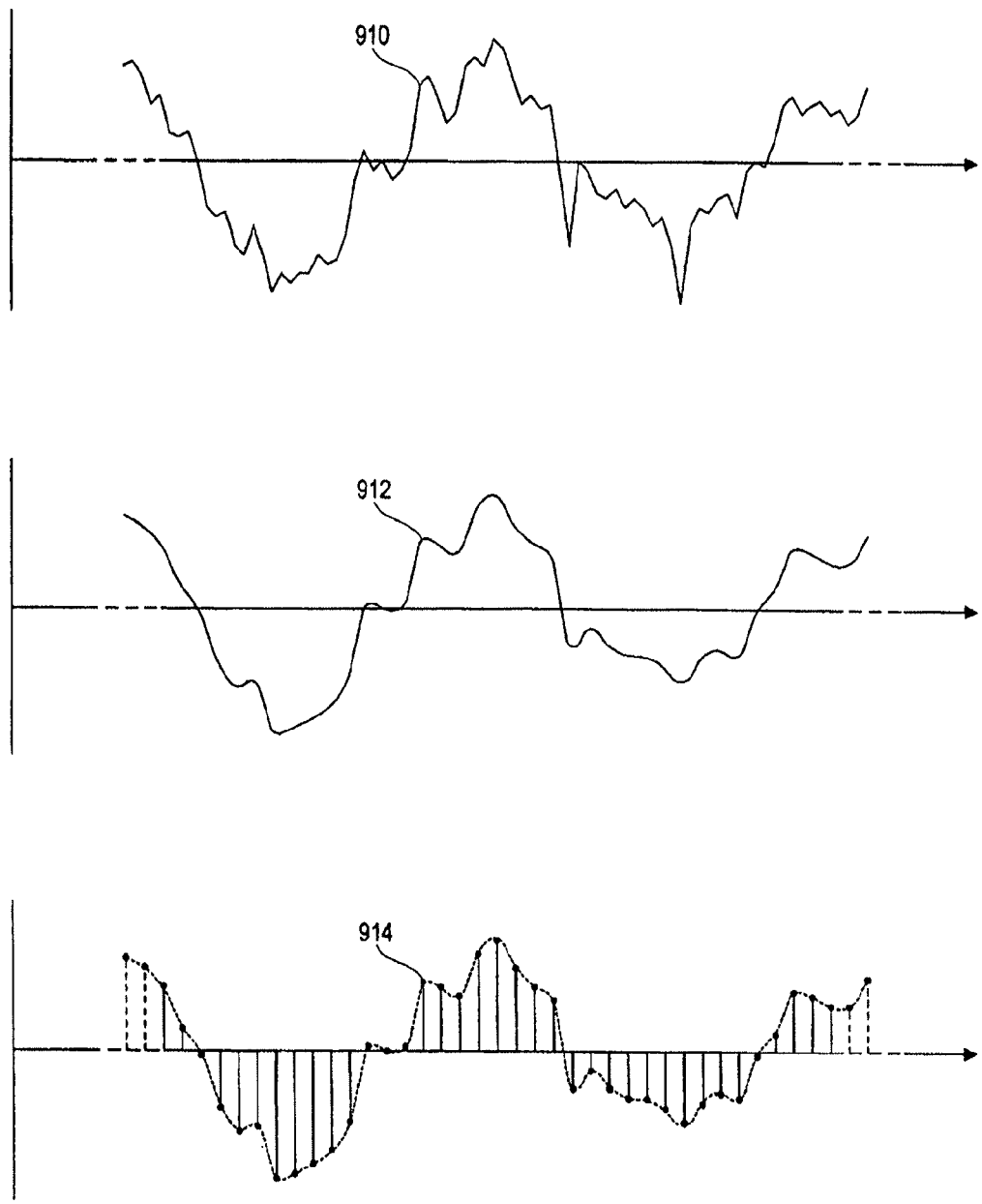
FIG. 9A is a graphical representation of an EEG signal illustrating the signal decomposed into time windows and samples.

FIG. 9A shows three different graphs of a waveform (amplitude vs. time) of the type that may be detected by the implantable devices 110 described herein. In the top graph of FIG. 9A, the waveform 910 is representative of an unprocessed EEG or ECoG waveform having a substantial amount of variability; the illustrated segment has a duration of approximately 160 ms and a dominant frequency (visible as the large-scale crests and valleys) of approximately 12.5 Hz. It will be recognized that the first waveform is rather rough and characterized by many peaks of small amplitude and duration; there is a substantial amount of high-frequency energy represented therein.

The middle graph of FIG. 9A shows the waveform of the top graph after it has been filtered to remove most of the high-frequency energy. In the middle graph, the waveform 912 is significantly smoother than the waveform 910 shown in the top graph. The filtering operation may be performed in the sensing front end 512 before the analog-to-digital converters 612 (FIG. 6). The filtered waveform 912 then can be sampled by one of the analog-to-digital converters 612. The result of such a sampling operation is represented graphically in the bottom waveform 914 shown in FIG. 9A. As illustrated, a sample rate used in one variation is 250 Hz (4.0 ms sample duration), resulting in approximately 40 samples over the illustrated 160 ms segment. As is well known in the art of digital signal processing, the amplitude resolution of each sample is limited. In FIG. 9A, each sample was measured with a resolution of 10 bits (or 1024 possible values). As is apparent upon visual analysis of the third waveform, the dominant frequency component has a wavelength of approximately 20 samples, which corresponds to the dominant frequency of 12.5 Hz. For sleep staging, a filtering operation may be performed in the sensing front end 512 before the analog-to-digital converters 612 (FIG. 6). For example, in sleep staging applications, a band pass filter may be set in the range of about 0.5 Hz to about 20 Hz.

Figure 9B:
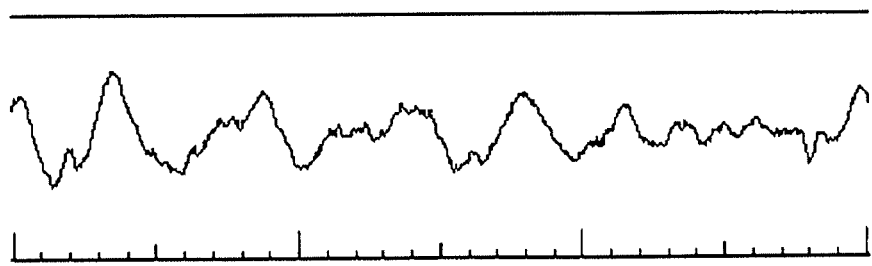
FIGS. 9B-9D are graphical representations of EEG signals that may be detected during stages of sleep.
Figure 9C:
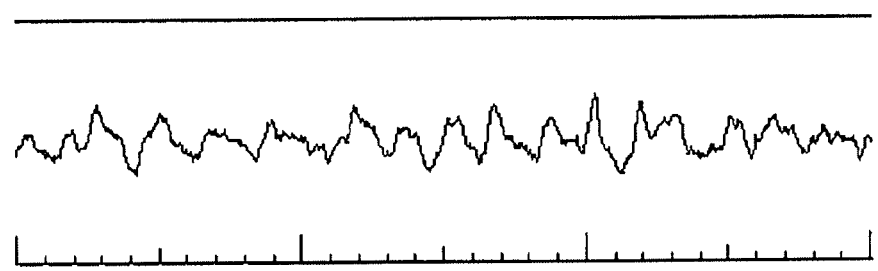
Figure 9D:
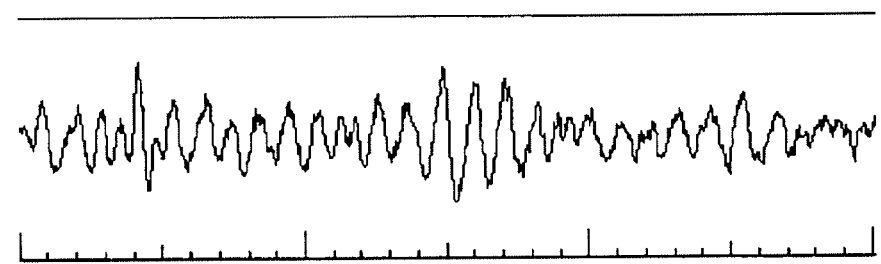

With respect to sleep staging, exemplary waveforms generally associated with a sleeping person are shown in FIGS. 9B-9D. In FIG. 9B, an ECoG tracing shows a slow delta wave 916 associated with sleep, FIG. 9C shows a theta wave 918, and FIG. 9D shows an alpha wave 920. Each waveform is approximately three seconds long. If a sampling rate of 250 Hz is used, each waveform results in approximately 750 samples. The dominant frequency component in each of FIGS. 9B, 9C, and 9D is approximately 2.5 Hz, 5.0 Hz and 10 Hz, respectively.

Method for Detecting Sleep Stages

Sleep is characterized by alternating periods of highly active rapid eye movement episodes (REM) and quiet non-REM (NREM) episodes, which are characterized by increased power in the low-frequency bands of the detectable EEG or EcoG waveforms. The implantable devices described here are capable of distinguishing between six discrete states or stages of sleep depth: wake (W), rapid eye movement (REM), stage 1 (S1), stage 2 (S2), stage 3 (S3), and stage 4 (S4), where S1 is a state of drowsiness or transition between wake and sleep, S2 is a state of light sleep, and S3 and S4 are two different stages characteristic of deep sleep. The implantable devices may include one or more sensors configured to sense (continuously or intermittently) the electrical activity of the brain or other physiological information. In some instances, the implantable devices may include at least two sensors for sensing physiological information. When at least two sensors are employed, the sensors may sense the same or different types of physiological information.

There are specific, well-known waveforms associated with EEG signals recorded during different sleep states and stages. For example, alpha, beta, theta, and delta waves are distinguished by the frequency ranges over which they occur and/or amplitude (alpha: 8-12 Hz, 20-100 microvolts; beta: 14-30 Hz and low voltage, on the order of 20 microvolts; theta: 4-7.5 Hz, usually under 20 microvolts; and delta: 0.5-3.5 Hz). Certain waveform morphology is also characterized by the term "k-complexes" (an EEG wave having a sharp negative front followed by a positive component) and "sleep spindles" (bursts of 12-14 Hz activity often occurring with a k-complex). There is a mix of alpha, beta, and higher frequency waveforms during wake. During Stage 1, alpha activity drops to less than 50% of the total power of the signal and transitions to theta. Stage 1 is usually brief, lasting about one to about seven minutes. Stage 2 is predominantly associated with theta activity with little to no alpha activity. Delta activity usually appears in less than 20% of the EEG record monitored during Stage 2 sleep. The amplitude of the waveforms may also increase from Stage 1. With respect to Stage 3, delta activity with high peak-to-peak amplitudes for about 20% to about 50% of the epoch, k-complexes, and spindles may be seen, and during Stage 4, slow delta activity for more than about 50% of the epoch may be seen. REM is associated with mixed frequency waveforms, slow alpha activity, and alpha spindles shorter than three seconds.

The method for detecting sleep stages disclosed herein is related to the Gotman system of analyzing EEG waveforms (J. Gotman, Automatic Seizure Detection: Improvements and Evaluation, *Electroencephalogr. Clin. Neurophysiol.* 76(4): 317-324 (1990)), as previously described in U.S. Pat. No. 6,810,285 to Pless et al., which is hereby incorporated by reference in its entirety. In the Gotman system, EEG waveforms are filtered and decomposed into "features" representing characteristics of interest in the waveforms. One such feature is characterized by the regular occurrence (i.e., density) of half waves that exceed a threshold amplitude occurring in a specified frequency band, especially in comparison to background activity.

Analyzing half wave activity can be used to detect when certain sleep stages are occurring. Much of the processing performed by the implantable devices described here involves operations on digital data in the time domain. To reduce the amount of data processing required by the implantable devices, preferably samples at ten-bit resolution are taken at a rate less than or equal to approximately 500 Hz (2.0 ms per sample).

Figure 10A:
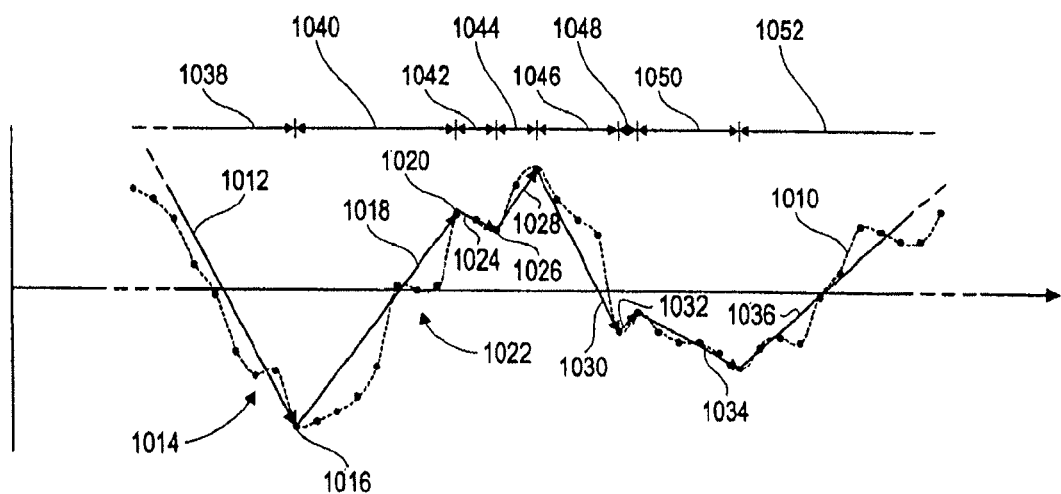
FIG. 10A is another graph of the EEG signal of FIG. 9A, illustrating half waves extracted from the signal.

Referring now to FIG. 10A, the processing of the wave morphology analysis units 712 is described in conjunction with a filtered and sampled waveform 1010 of the type illustrated as the bottom waveform 914 shown in FIG. 9A. In a first half wave 1012, which is partially illustrated in FIG. 10A (the starting point occurs before the illustrated waveform segment 1010 begins), the waveform segment 1010 is essentially monotonically decreasing, except for a small first perturbation 1014. Accordingly, the first half wave 1012 is represented by a vector from the starting point (not shown) to a first local extremum 1016, where the waveform starts to move in the opposite direction. The first perturbation 1014 is of insufficient amplitude to be considered a local extremum, and is disregarded by a hysteresis mechanism (discussed in further detail below). A second half wave 1018 extends between the first local extremum 1016 and a second local extremum 1020. Again, a second perturbation 1022 is of insufficient amplitude to be considered an extremum. Likewise, a third half wave 1024 extends between the second local extremum 1020 and a third local extremum 1026; this may appear to be a small perturbation, but is greater in amplitude than a selected hysteresis threshold. The remaining half waves 1028, 1030, 1032, 1034, and 1036 are identified analogously. As will be discussed in further detail below, each of the identified half waves 1012, 1018, 1024, 1028, 1030, 1032, 1034, and 1036 has a corresponding duration 1038, 1040, 1042, 1044, 1046, 1048, 1050, and 1052, respectively, and analogously, a corresponding amplitude determined from the relative positions of each half wave's starting point and ending point along the vertical axis, and a slope direction, either increasing or decreasing.

In one variation, the method allows for a programmable hysteresis setting in identifying the ends of half waves. In other words, as explained above, the end of an increasing or decreasing half wave might be prematurely identified as a result of quantization (and/or other noise, low-amplitude signal components, and other perturbing factors), unless a small hysteresis allowance is made before the reversal of the waveform direction is recognized and a corresponding half wave end is identified. Hysteresis allows for insignificant variations in signal level that are inconsistent with the signal's overall movement to be ignored without the need for extensive further signal processing such as filtering. Without hysteresis, such small and insignificant variations might lead to substantial and gross changes where half waves are identified, leading to unpredictable results.

Figure 10B:
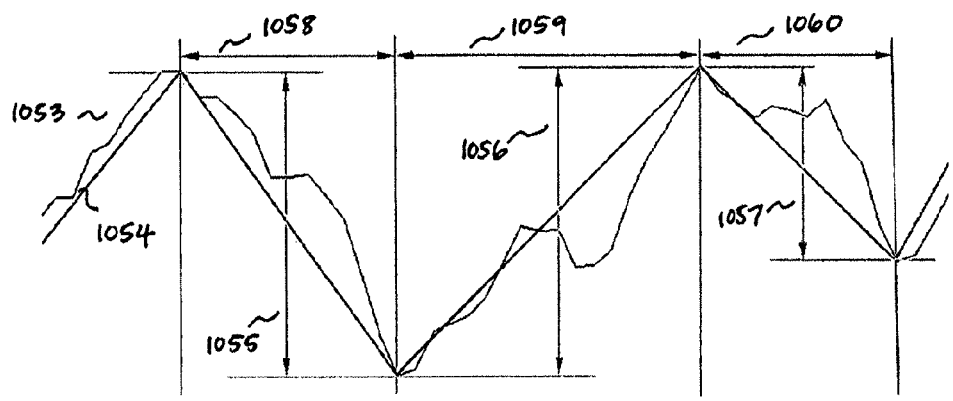
FIG. 10B is a graph of an ECoG signal, illustrating minimum and maximum signal amplitudes and durations.
Figure 12:
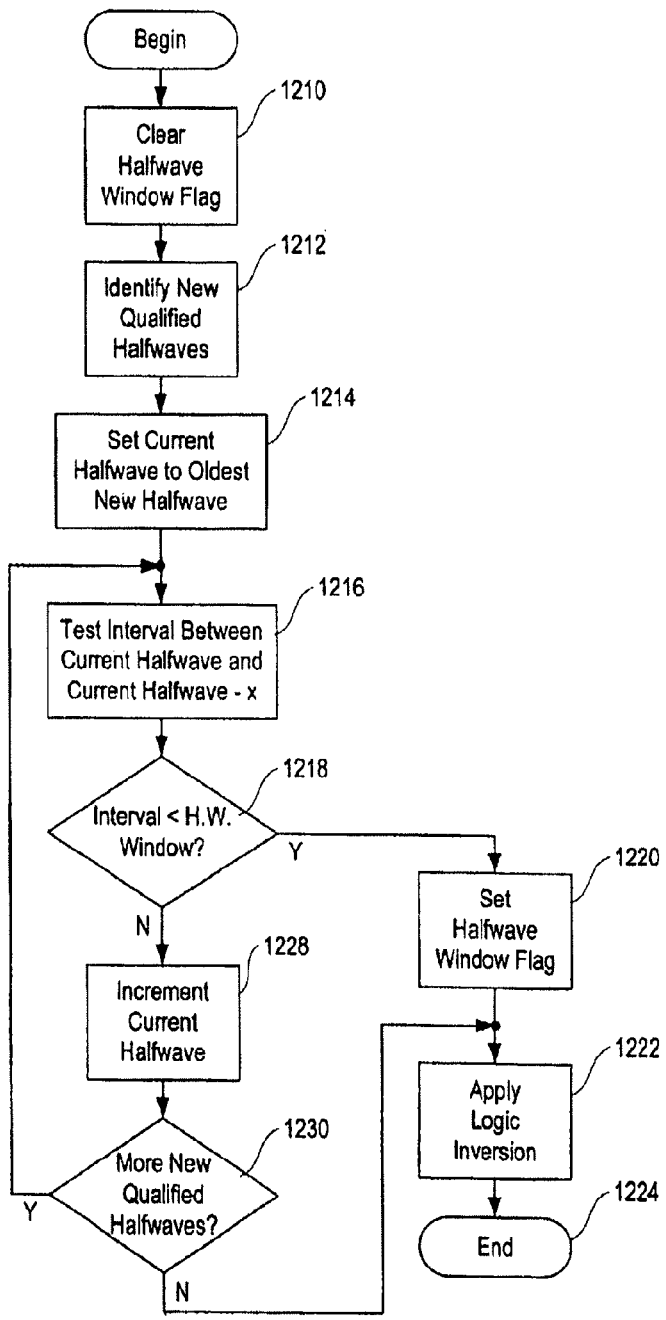
FIG. 12 is a flow chart of a method of analyzing half waves from an EEG signal

In one variation of sleep stage detection, if both the amplitude and duration qualify by exceeding a corresponding preset minimum threshold and qualify by not exceeding a preset maximum threshold, then the amplitude, duration, half-wave time, and half-wave direction are stored in a buffer. Adding a maximum half-wave width parameter can further specify the minimum frequency in a range of frequencies. A maximum amplitude threshold allows the exclusion of high amplitude half waves that are often characteristic of seizures or other non-sleep activity. For example, as shown in FIG. 10B, the half wave with an amplitude 1055 and duration 1058 may be classified as a theta-type half wave, whereas a half wave with an amplitude 1056 and duration 1059 may be classified as a delta-type half wave. The half wave with amplitude 1057 and duration 1060 may not satisfy the necessary amplitude criterion so it is not included in any histogram that might be generated using the data acquired or processed.

Processing that can be performed with regard to the waveform 1010 and half waves shown in FIGS. 10A and 10B is illustrated in a flow chart in FIG. 11. First, an increasing half wave is identified (i.e., a half wave with an ending amplitude that is higher than its starting amplitude), as in the second half wave 1018 of FIG. 10A. To accomplish this, initial values are assigned to several variables, namely, half-wave time (1110) (half-wave time corresponds to the time that elapses between adjacent qualifying half waves), half-wave duration, peak amplitude, first sample value, and ending threshold (1112). Specifically, the half-wave time and half-wave duration value is set to zero; the peak amplitude and first sample values are set to the amplitude value of the last-observed sample (which, as described above, is a value having 10-bit precision); and the ending threshold is set to the last observed sample minus a small preset hysteresis value.

When an EEG sample is acquired (1114), the half-wave time and half-wave duration variables are incremented (1116). If amplitude of the EEG sample is greater than the value of the peak amplitude variable (1118), then the amplitude of the half wave is increasing. If the half wave is increasing, the peak amplitude variable is reset to correspond to the amplitude of the EEG signal and the ending threshold is reset to a value corresponding to the amplitude of the EEG signal less a predetermined small hysteresis value, and the next EEG sample is awaited (1114). If the amplitude of the EEG sample is less than the ending threshold (1122), then the hysteresis value has been exceeded, and a local extremum has been identified. Accordingly, the end of the increasing half wave has been reached. At this point, the amplitude and duration of the half wave are calculated (1124). The amplitude of the half wave is the peak amplitude minus the amplitude of the first EEG sample value, and the duration is simply the duration of the detected half wave. If the local extremum is not yet identified, the next EEG sample is awaited and the process is repeated on that sample (1114). In one variation, if both the amplitude and the duration qualify by both exceeding corresponding preset minimum thresholds but not exceeding preset maximum thresholds (1126), then the amplitude, duration, half-wave time, and half-wave direction (increasing) are stored in a buffer (1128), and the half-wave time is reset to zero (1130). However, in other variations (not shown), multiple amplitude and duration threshold comparisons might be simultaneously performed on the same half wave to simultaneously determine delta, theta, and alpha components. For example, and referring now to FIG. 10B, a half wave with illustrated amplitude 1056 and duration 1059 may not satisfy the criterion for alpha, but may satisfy the criterion for theta. The parameters for this half wave may then be stored in a buffer for theta. Multiple buffers may also be provided to store parameters, e.g., if different frequency bands are employed. In another variation, multiple half-wave detectors may be configured to run in parallel so that parameters for each detector correspond to a specific frequency band.

Once an increasing half wave is detected, the half-wave duration, the peak amplitude, the first sample value, and ending threshold variables are initialized again (1132). Half-wave duration is set to zero, the peak amplitude and the first sample value are set to the most recent sample value, and the ending threshold is set to the last sample value plus the hysteresis value and the next EEG sample is awaited (1134), the half-wave time and half-wave duration variables are incremented (1136). If the amplitude of the EEG sample is lower than the peak amplitude (1138), then the direction of the half wave is decreasing. Accordingly, the peak amplitude is reset to the amplitude of the current EEG sample, and the ending threshold is reset to correspond to the amplitude of the current EEG sample plus the hysteresis value (1140), and the next sample is awaited (1134).

If the amplitude of current EEG sample is greater than the ending threshold (1142), then the hysteresis value has been exceeded, and a local extremum has been identified. Accordingly, the end of the decreasing half wave has been reached, and the amplitude and duration of the half wave are calculated (1144). The amplitude is the first sample value minus the peak amplitude, and the duration is the duration of the half wave in the current EEG sample. If the extremum is not identified, the next EEG sample is awaited (1134). If both the amplitude and the duration qualify by exceeding corresponding preset minimum thresholds but not exceeding a preset maximum thresholds (1146), then the amplitude, duration, half-wave time, and half-wave direction (decreasing) are stored in a buffer (1148), and the half-wave time is reset to zero (1150).

Once a decreasing half wave is identified, the above-described operations are repeated to identify additional half waves (1112). Parameters corresponding to qualifying half waves, including their directions, durations, amplitudes, and the elapsed time between adjacent qualified half waves (i.e., the half-wave time variable) are stored. Half wave detection is an ongoing and continuous process, but the half wave detection operations may be suspended from time to time when conditions or device state call for it, e.g. when the implantable device is inactive or, if the implantable device is configured to deliver stimulation or some other therapy, when the stimulation or the other therapy is being performed. The half wave detection procedure can be resumed after it has been suspended at the first initialization operation (1110).

In one variation, to reduce power consumption, the half wave detection operations are performed in customized electronic hardware. Preferably, the operations of FIG. 11 are performed in parallel whenever the wave morphology analysis units 712 (FIG. 7) are active.

Software operations can also be carried out on a periodic basis to provide useful information about the physiological information being monitored. In one variation, and referring now to FIG. 12, the stored information associated with the qualifying half waves is processed to define sleep states or stages by the ratio or absolute quantity of delta, theta or alpha waves detected within a certain period of time. More specifically, the software process involves clearing a half-wave window flag (1210), identifying the qualifying half waves detected during the chosen period of time (1212), associating a "current half wave" variable with the oldest detected half wave in the chosen period of time (1214), and using a histogram counter to track the time interval between the most recent half wave detected and prior detected half waves (1216). The chosen period of time can be a defined processing window (e.g., a recurring time interval that is either fixed or programmable). For example, a 128 ms processing window may be selected which, at a 250 Hz sampling rate, would be expected to correspond to 32 EEG samples.

The histogram counter tracks the time interval between the most recent half wave detected and the prior half waves, where x1 is the number of half waves to be identified within a selected half-wave time window (the duration of the half-wave time window is another programmable value) for the first event detector 812, and x2 is the number of half waves within the same half-wave time window for the second event detector 816, and likewise for x3 and the third event detector 822. Detection of an event may be defined as the occurrence of the condition when x1 is greater than a prespecified value, or when the ratio of any combination of x (e.g., x1 and x2) is greater than a prespecified value.

A histogram counter may be included in the detection subsystem (FIG. 4) to keep track of the detections within each frequency band, providing a measure of the average low-frequency power in the signal over a period of time. The number detections within each frequency band over a specified time window (for example, a sliding window of 1-10 minutes) then could be used to classify which sleep stage occurred for that time period. Transitions are noted when the number of detections within one band decreases and in another band increases.

Figure 23:
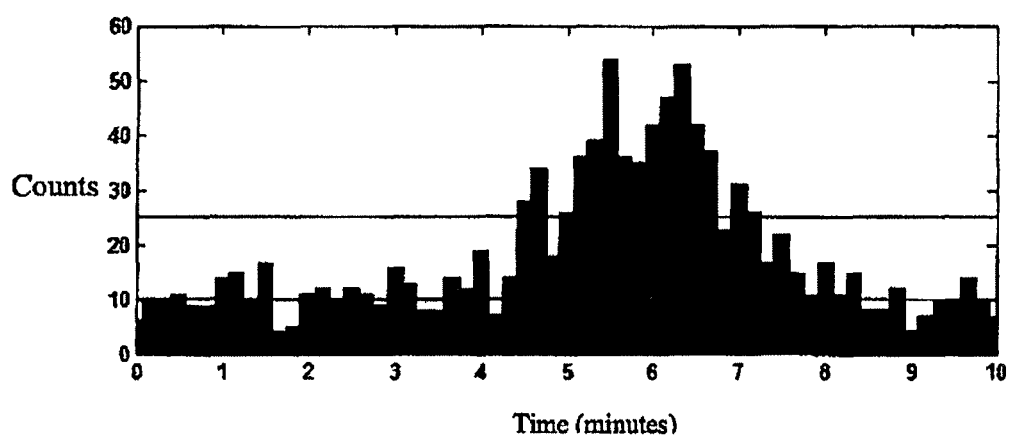
FIG. 23 is a histogram of delta half-wave counts, where x-axis variable is time and the y-axis variable is the delta half-wave counts.

Sleep stages may be detected by using a set of low frequency half-wave counters simultaneously detecting waveforms in the EEG samples. For example, these counters may be set up to detect the waveform activity in the frequency range of 0.5 Hz-3.5 Hz for the delta band, 4.0 Hz-7.5 Hz for the theta band, and 8.0 Hz-12 Hz for the alpha band. Line length and area detectors may also be implemented to measure the overall complexity and power of the signal. Sleep stages may then be characterized by the ratio or absolute quantity of delta, theta, alpha within a period of time. For example, in the histogram shown in FIG. 23, the number of delta half wave counts (on the y-axis) are binned into brief time windows (on the x-axis) between about 10 seconds to about one minute. When the number of half waves within a window exceeds a threshold x, a particular sleep stage may be detected. For example, if between about 10 and about 25 delta half waves are detected in a 10 second window, then sleep Stage 3 is detected; and if greater than 25 delta half waves are detected per 10 second window, then sleep Stage 4 is detected. REM, wake, and sleep Stages 1 and 2 may be determined in a similar manner by characterization of alpha and theta waves. The thresholds may be independently adjusted to optimally tune the sleep stage detector to each individual patient. Algorithms, such as one that calculates the ratio between different frequency bands (e.g., the ratio between delta and theta), may also be employed.

The event detectors may be configured in any manner suitable to monitor sleep or detect sleep states or stages. In one variation, a single wave morphology analysis unit is used to detect half waves. In another variation, where multiple waveform morphology analysis are used, they may be set up in parallel to each frequency band of interest. Half waves within a specific duration and amplitude range may then be binned into appropriate bins in a histogram.

The time interval between the most-recently detected half wave and x previously-detected half waves is then tested against a selected half-wave time window (1216), where x is a specified minimum number of half waves (preferably a programmable value) to be identified within the half-wave time window The half-wave time window is desirably selected to correspond to the time over which detection of a certain sleep state or stage, or might be expected to occur. If the measured time interval is less than the half-wave time window (1218), then the half-wave window flag is set (1220). Logic inversion is then selectively applied (1222) to determine whether a wave morphology analysis unit (or other analyzer) is triggered by the presence or absence of a condition, as explained in greater detail below. If the measured time interval is greater than or equal to the half-wave time window, the value of the half wave pointer is incremented to point to the next new half wave (1228). If there are no more new half waves (1230), logic inversion is applied if desired (1222), and the procedure ends (1224). If there are more new half waves, the next time interval is tested (1216) and the process continues from there.

Logic inversion allows the output flag for the wave morphology analysis unit (or any other analyzer) to be selectively inverted. If logic inversion is applied to an output of a particular analysis unit, then the corresponding flag will remain cleared when the detection criterion (e.g., number of qualifying half waves) is met, and will be set when the detection criterion is not met. This capability provides some additional flexibility in configuration, facilitating detection of the absence of certain signal characteristics when, for example, the presence of those characteristics is the norm.

Figure 13:
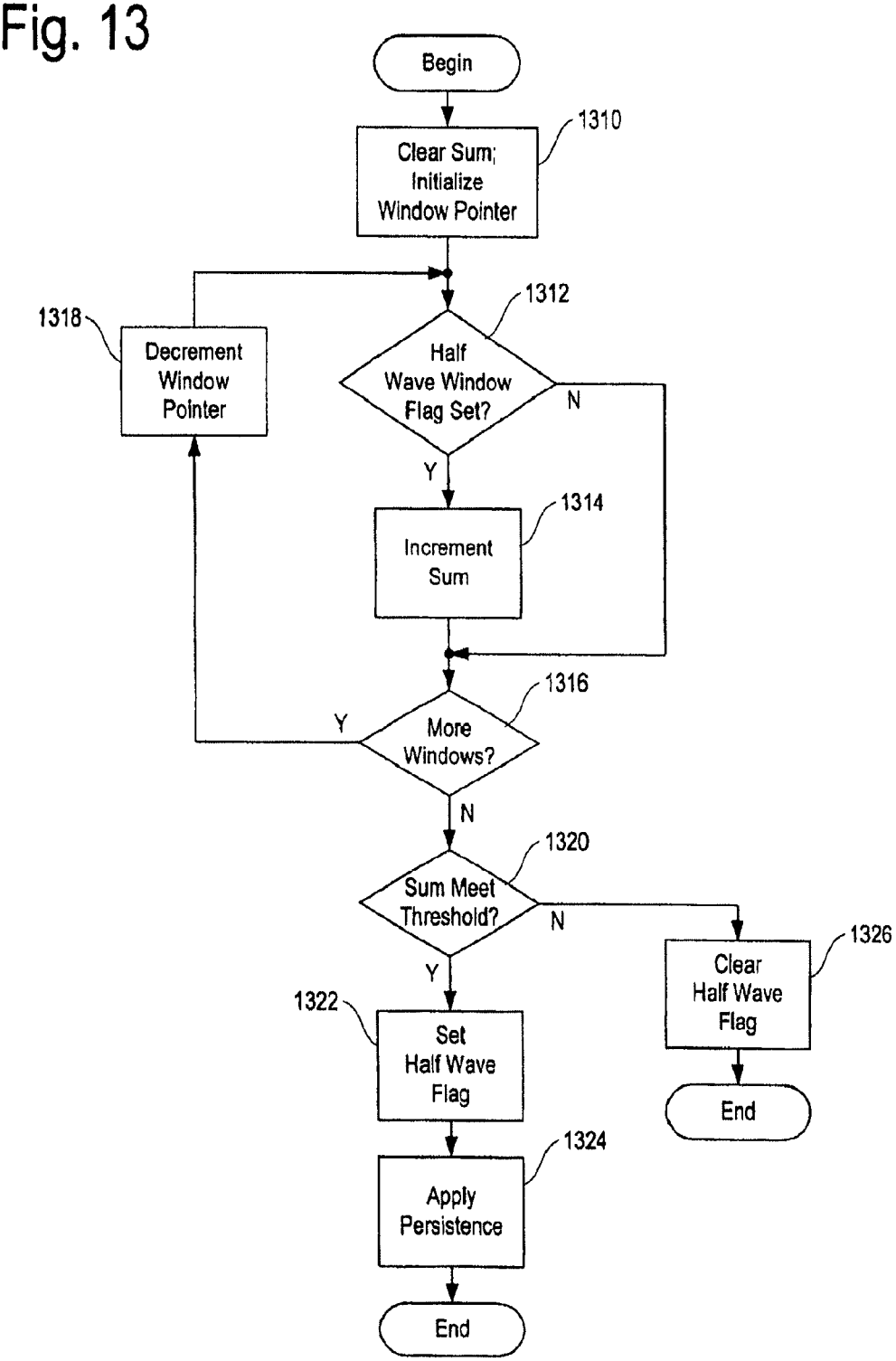
FIG. 13 is a flow chart of a method of applying an X of Y criterion to half-wave windows using a central processing unit.

In one variation, the half-wave window flag is used to indicate whether the number of qualifying half waves exceeding a predetermined value has occurred over an interval the endpoint of which corresponds to the end of the most recent processing window. To reduce the occurrence of spurious detections, an X-of-Y criterion is applied to prevent triggering the wave morphology analysis unit unless a sufficient number of qualifying half waves occur in X of the Y most recent processing windows, where X and Y are parameters individually adjustable for each analysis unit. Referring now to FIG. 13, a sum representing recent processing windows in which the half-wave window flag was set is cleared to zero and a current window pointer is initialized to point to the most recent processing window (1310). If the half-wave window flag corresponding to the current window pointer is set (1312), then the sum is incremented (1314). If there are more processing windows to examine (for an X-of-Y criterion, a total of Y processing windows, including the most recent, should be considered) (1316), then the window pointer is decremented (1318) and the flag testing and sum incrementing steps (1312-1314) are repeated. After Y windows have been considered, if the sum of windows having set half-wave window flags meets the threshold X (1320), then the half-wave analysis flag is set (1322), persistence (described below) is applied (1324), and the procedure is complete. Otherwise, the half wave analysis flag is cleared (1326).

Persistence, another per-analysis-tool setting, allows the effect of an event detection (a flag set) to persist beyond the end of the detection window in which the event occurs. Persistence may be set anywhere from one to fifteen seconds (though other settings are possible), so if detections with multiple analysis tools (e.g., multiple wave morphology analysis units or multiple event detectors) do not all occur simultaneously (though they should still occur within a fairly short time period), a Boolean combination of flags will still yield positive results. Persistence can also be used with a single analysis tool to smooth the results.

When the process of FIG. 13 is completed, the half-wave analysis flag (set or cleared in steps 1322 and 1326, respectively) indicates whether an event has been detected in the corresponding channel of the wave morphology analysis units 712 or, stated another way, whether a sufficient number of qualifying half waves have appeared in X of the Y most recent processing windows. Although in the variations shown in FIGS. 12 and 13, the operations are performed in software, it should be recognized that some or all of those steps can be performed using customized electronics, if it proves advantageous in the desired application to use such a configuration (e.g., to optimize the computational power that is required to carry out the operations in the implantable device).

In some instances, it may be desirable to include either or both a line length detector and an area detector for sleep staging. For example, these features may be useful when the amplitude of the EEG sample is high and/or the signal is complex, as may occur during the REM stage or during deep sleep or "slow wave" sleep (Stages 3 and 4). In the instances of increasing amplitude, the high amplitude of the slow wave may be detected using an area detector alone or in combination with a half wave detector. Similarly, in REM sleep there may be an increase in signal complexity that can be detected using a line length detector alone or in conjunction with a half wave detector.

Figure 14:
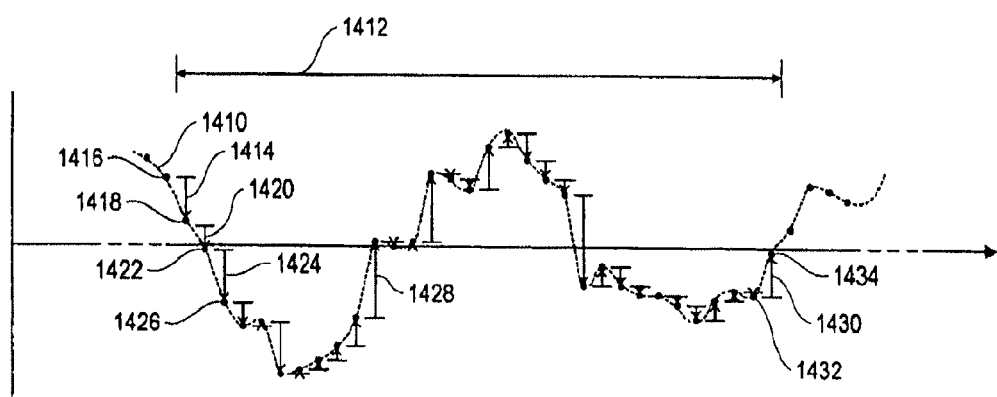
FIG. 14 is a graph of the EEG signal of FIG. 9A, illustrating a line-length function calculation.

FIG. 14 illustrates the filtered waveform of FIG. 9A, further depicting line lengths identified within a time window. The time window selected may be the same as or different from the selected half-wave processing window. From an implementation standpoint, a single device interrupt upon the conclusion of each processing window allows all of the analysis tools to perform the necessary corresponding software processes; the line length analysis process of FIG. 16 (described below) is one such example. The waveform 1410 shown in FIG. 14 is a filtered and otherwise preprocessed EEG signal as received by one of the window analysis units 714 from the sensing front end 512. As discussed above, line lengths are considered within time windows. The duration of the time window 1412 shown in FIG. 14 is 128 ms which, at a 250 Hz sampling rate corresponds to an expected 32 samples. Other time windows and sampling rates can be specified as appropriate.

The total line length for the time window 1412 is the sum of the sample-to-sample amplitude differences within that window 1412. For example, the first contribution to the line length within the window 1412 is a first amplitude difference 1414 between a previous sample 1416 occurring immediately before the window 1412 and a first sample 1418 occurring within the window 1412. The next contribution comes from a second amplitude difference 1420 between the first sample 1418 and a second sample 1422; a further contribution 1424 comes from a third amplitude difference between the second sample 1422 and a third sample 1426, and so on. At the end of the window 1412, the final contribution to the line length comes from a last amplitude difference 1430 between a second-last sample 1432 in the window 1412 and a last sample 1434 in the window 1412. Note that all line lengths, whether increasing or decreasing in direction, are accumulated as positive values. A decreasing amplitude difference 1414 and an increasing amplitude difference 1428 therefore both contribute to a greater line length.

Figure 15:
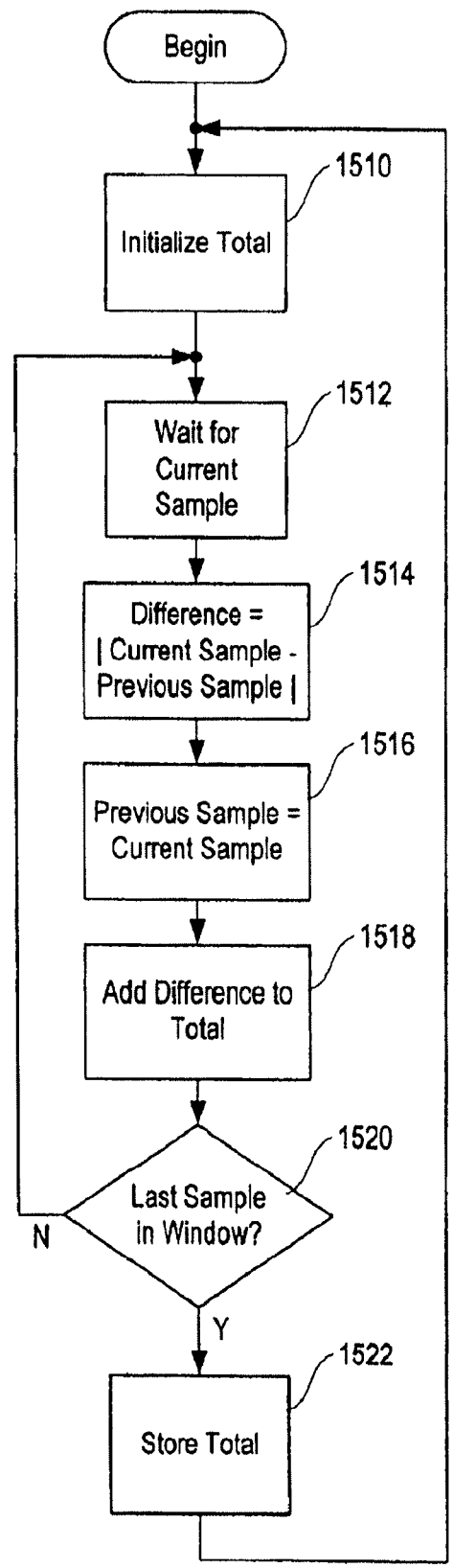
FIG. 15 is a flow chart of a method of calculating the line-length function of FIG. 14 using the waveform analyzer of FIG. 7.

The flow chart of FIG. 15 describes how the line length is calculated. At the beginning of a time window, a "line length total" variable is initialized to zero (1510). An EEG sample is awaited (1512), and the absolute value of the difference in amplitude between the current EEG sample and the previous EEG sample (which, when considering the first sample in a window, may come from the last sample in a previous window) is measured (1514). Then, the previous sample (if any) is replaced with the value of the current sample (1516), and the calculated absolute value is added to the total (1518). If there are more samples remaining in the window 1412 (1520), another current sample is awaited (1512) and the method continues. Otherwise, the line length calculation for the window 1412 is complete, and the total is stored (1522), the total is reinitialized to zero (1510), and the method continues.

In other variations, either the measured amplitude difference (calculated as described above (1514)) or the sample values used to calculate the measured amplitude difference may be mathematically transformed in useful nonlinear ways. For example, it may be advantageous in certain circumstances to calculate the difference between adjacent samples using the squares of the sample values, or to calculate the square of the difference between sample values, or both. It is contemplated that other transformations (such as square root, exponentiation, logarithm, and other nonlinear functions) might also be advantageous in certain circumstances. Whether such a transformation is performed and the nature of any transformation to be performed preferably are programmable parameters of the implantable device 110.

As with the half wave analysis method set forth above, the line length calculation does not need to terminate, rather, it can be configured to be free-running yet interruptible. If the line length calculation is restarted after having been suspended, it should be reinitialized and restarted at the beginning of a time window. This synchronization maybe accomplished through hardware interrupts.

Figure 16:
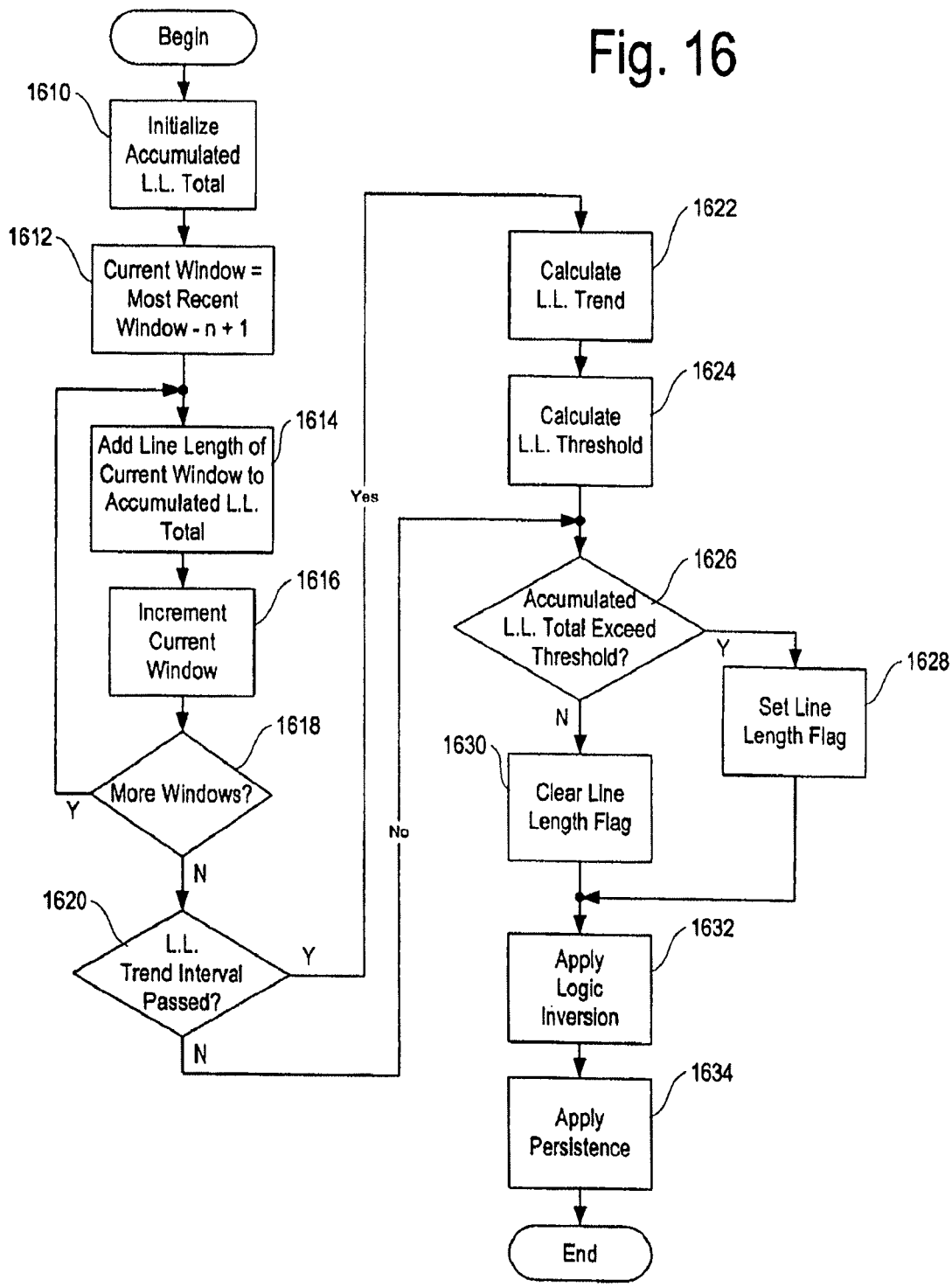
FIG. 16 is a flow chart of a method of calculating and analyzing a line-length function of an EEG signal

Referring now to the flow chart of FIG. 16, the calculated line lengths are further processed after the calculations for each time window 1412 are obtained and stored. The process begins by calculating a running accumulated line length total over a period of n time windows. Where n>1, the effect is that of a sliding window. (Indeed, in one variation, true sliding-window processing is used). The accumulated total variable is first initialized to zero (1610). A current window pointer is set to indicate the nth to the last window, i.e., the window (n−1) windows before the most recent window (1612). The line length of the current window is added to the total (1614), the current window pointer is incremented (1616), and if there are more windows between the current window pointer and the most recent (last) window (1618), the adding and incrementing steps (1614-1616) are repeated. Accordingly, by this method, the resulting total includes the line lengths for each of the n most recent windows.

In one variation, the accumulated total line length is compared to a dynamic threshold, which is based on a trend of recently observed line lengths. The trend is recalculated regularly and periodically, after each recurring line-length trend interval (which is preferably a fixed or programmed time interval). Each time the line-length trend interval passes (1620), the line length trend is calculated or updated (1622). In one variation, this is accomplished by calculating a normalized moving average of several trend samples, each of which represents several consecutive windows of line lengths. A new trend sample is taken and the moving average is recalculated upon every line length trend interval. The number of trend samples used in the normalized moving average and the number of consecutive windows of line length measurements per trend sample both are preferably fixed or programmable values.

After the line length trend has been calculated, the line length threshold is calculated (1624) based on the new line length trend. The threshold may be set as either a percentage of the line length trend (either below 100% for a threshold that is lower than the trend or above 100% for a threshold that is higher than the trend) or alternatively as a fixed numeric offset from the line length trend (either negative for a threshold that is lower than the trend or positive for a threshold that is higher than the trend). It should be observed that other methods for deriving a numeric threshold from a numeric trend are possible.

The first time the process of FIG. 16 is performed, there is generally no line length trend against which to set a threshold. Accordingly, for the first several passes through the process (until a sufficient amount of EEG data has been processed to establish a trend), the threshold is essentially undefined and the line length detector should not return a positive detection. Some "settling time" is required to establish trends and thresholds before a detection can be made. If the accumulated line length total exceeds the calculated threshold (1626), then a flag is set (1628) indicating a line-length-based event detection on the current window analysis unit channel 714. As described above, the threshold is dynamically calculated from a line length trend, but alternatively, the threshold may be static, either fixed or programmed into the implantable device 110. If the accumulated line length total does not exceed the threshold, the flag is cleared (1630).

Once the line length flag has been either set or cleared, logic inversion is applied (1632), persistence is applied (1634), and the procedure terminates. The resulting persistent line length flag indicates whether the threshold has been exceeded within one or more windows over a time period corresponding to the line length flag persistence. As will be discussed in further detail below, line length event detections can be combined with the half-wave event detections, as well as any other applicable detection criteria.

Figure 17:
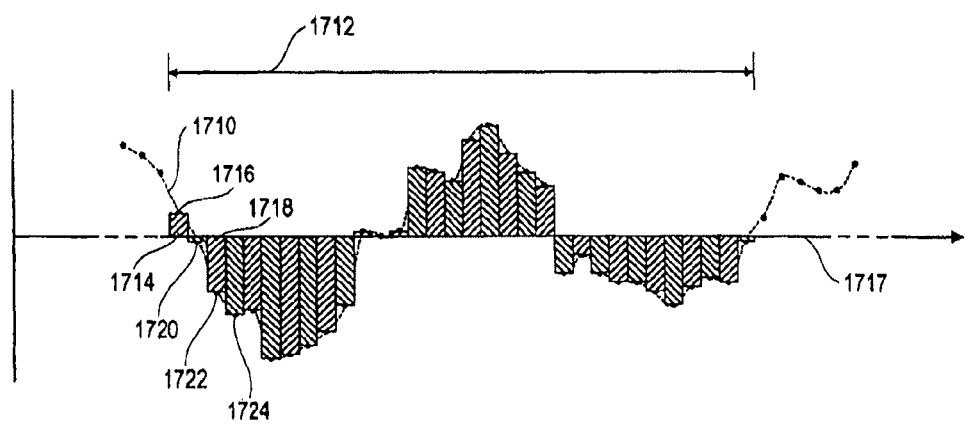
FIG. 17 is a graph of the EEG signal of FIG. 9A, illustrating an area function calculation.

FIG. 17 illustrates the filtered waveform of FIG. 9A with area under the curve identified within a window. Area under the curve, which in some circumstances is somewhat representative of a signal's energy (though energy of a waveform is more accurately represented by the area under the square of a waveform), may be another criterion for detecting certain events occurring with respect to the physiological information being monitored by the implantable device. In FIG. 17, the total area under the curve represented by a waveform 1710 within the window 1712 is equal to the sum of the absolute values of the areas of each rectangular region of unit width vertically bounded by the horizontal axis and the EEG sample. For example, the first contribution to the area under the curve within the window 1712 comes from a first region 1714 between a first sample 1716 and a baseline 1717. A second contribution to the area under the curve within the window 1712 comes from a second region 1718, including areas between a second sample 1720 and the baseline 1717. There are similar regions and contributions for a third sample 1722 and the baseline 1717, a fourth sample 1724 and the baseline 1717, and so on. (From a mathematical standpoint, the region widths are not significant to the area calculation; rather, the area can be considered the product of the amplitude or the region and a region unit width, which can be disregarded.) Although the concept of separate rectangular regions is a useful construct for visualizing the idea of area under a curve, any process for calculating area need not partition areas into regions as such regions are shown in FIG. 17.

Figure 18:
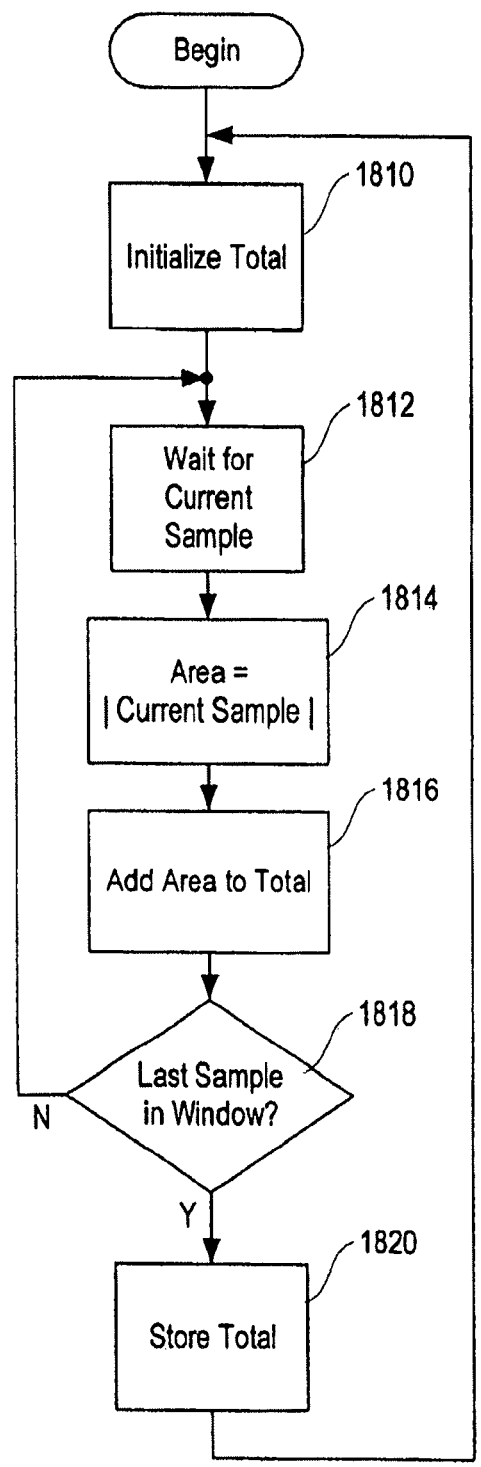
FIG. 18 is a flow chart of a method FIG. 7 of calculating an area function as illustrated in FIG. 17 using the waveform analyzer or FIG. 7.

Referring now to the flow chart of FIG. 18, the areas under the curve shown in the graph of FIG. 17 are calculated using a process that is invoked at the beginning of a time window. Initially, an "area total" variable is initialized to zero (1810). The current EEG sample is awaited (1812), and the absolute value of the current EEG sample is measured (1814). As with the line length calculation method described above in other variations, the current EEG sample may be mathematically transformed in useful nonlinear ways. For example, it may be advantageous in certain circumstances to calculate the square of the current sample rather than its absolute value. The result of such a transformation by squaring each sample will generally be more representative of signal energy, though it is contemplated that other transformations (such as square root, exponentiation, logarithm, and other nonlinear functions) might also be advantageous in certain circumstances. Whether such a transformation is performed and the nature of any transformation performed both preferably are programmable parameters of the implantable device 110.

The calculated absolute value is added to the total (1816). If there are more EEG samples remaining in the window 1712 (step 1818), another current sample is awaited (1812) and the process continues. Otherwise, the area calculation for the window 1712 is complete, and the total is stored (1820), the total is reinitialized to zero (1810), and the method continues. As with the half wave and line length analysis methods set forth above, the area calculation does not need to terminate, rather, it can be configured to be free-running yet interruptible. If the area calculation is restarted after having been suspended, it should be reinitialized and restarted at the beginning of a window. This synchronization can be accomplished through hardware interrupts.

Figure 19:
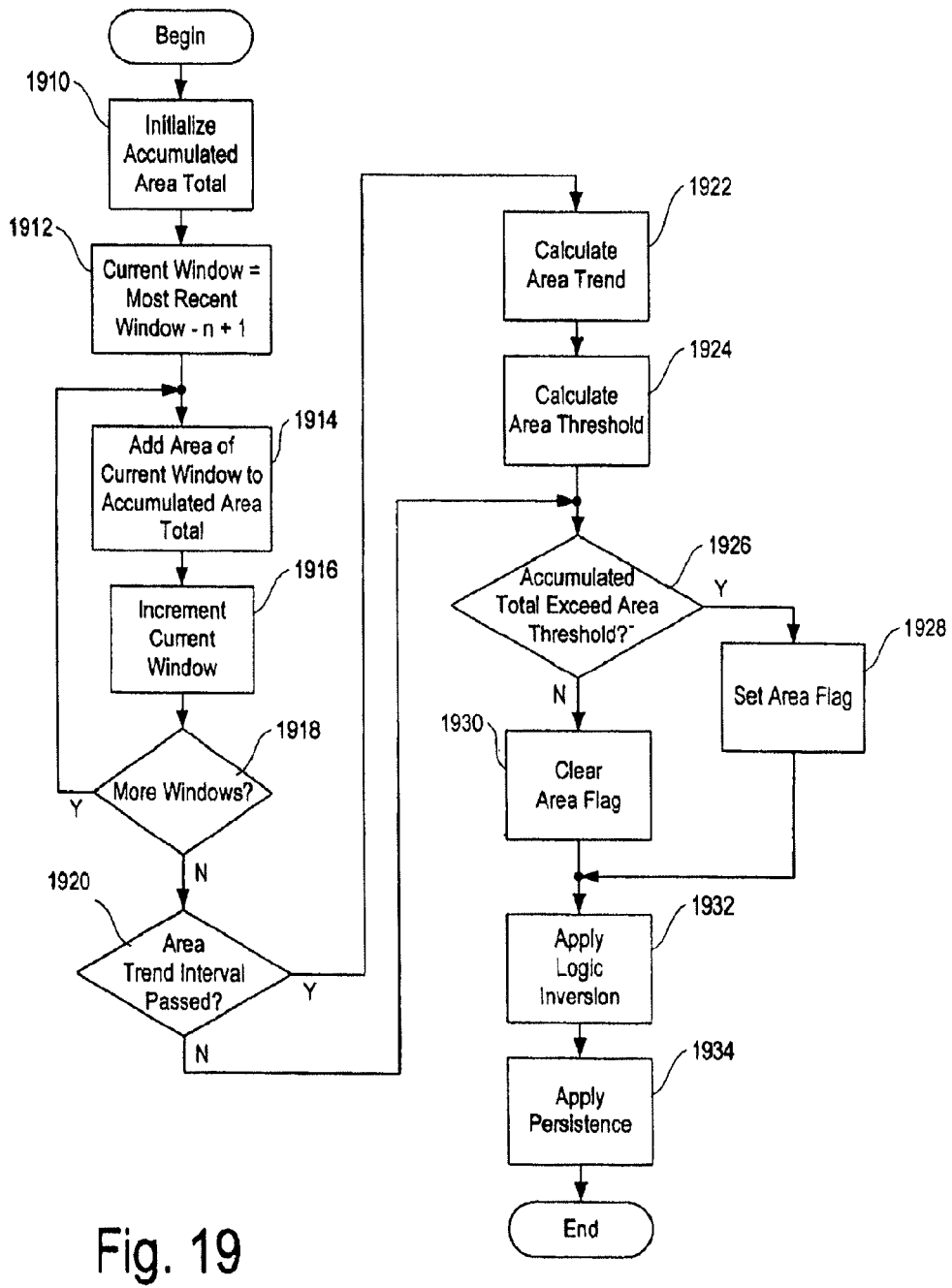
FIG. 19 is a flow chart of a method of calculating and analyzing an area function of an EEG signal

Referring now to the flow chart of FIG. 19, the area calculations are processed. As is accomplished for the line length calculations, the area detection method begins by calculating a running accumulated area total over a period of n time windows. Again, where n>1, the effect is that of a sliding window. The accumulated total is initialized to zero (1910). A current window pointer is set to indicate the nth to the last window, i.e., the window (n−1) windows before the most recent window (1912). The area for the current window is added to the total (1914), the current window pointer is incremented (1916), and if there are more windows between the current window and the most recent (last) window (1918), the adding and incrementing steps (1914-1916) are repeated. Accordingly, by this process, the resulting total includes the areas under the curve for each of the n most recent windows.

In one variation, the accumulated total area is compared to a dynamic threshold, which is based on a trend of recently observed areas. The trend is recalculated regularly and periodically, after each recurring area trend interval (which is preferably a fixed or programmed time interval). Each time the area trend interval passes (1920), the area trend is calculated or updated (1922). In one variation, this is accomplished by calculating a normalized moving average of several trend samples, each of which represents several consecutive windows of areas. A new trend sample is taken and the moving average is recalculated upon every area trend interval. The number of trend samples used in the normalized moving average and the number of consecutive windows of area measurements per trend sample both are preferably fixed or programmable values.

After the area trend has been calculated, the area threshold is calculated (step 1924) based on the new area trend. As with line length, discussed above, the threshold may be set as either a percentage of the area trend (either below 100% for a threshold that is lower than the trend or above 100% for a threshold that is higher than the trend) or alternatively a fixed numeric offset from the area trend (either negative for a threshold that is lower than the trend or positive for a threshold that is higher than the trend).

Again, as is the case with the line length detection method, the first time the process described in FIG. 19 is performed, there is generally no area trend against which to set a threshold. Accordingly, for the first several passes through the process (until a sufficient amount of EEG data has been processed to establish a trend), the threshold is essentially undefined and the area detector should not return a positive detection. Some "settling time" is required to establish trends and thresholds before a detection can be made.

If the accumulated total exceeds the calculated threshold (1926), then a flag is set (1928) indicating an area-based event detection on the current window analysis unit channel 714. Otherwise, the flag is cleared (1930). Once the area flag has been either set or cleared, logic inversion is applied (1932), persistence is applied (1934), and the procedure terminates. The resulting persistent area flag indicates whether the threshold has been exceeded within one or more windows over a time period corresponding to the area flag persistence. As will be discussed in further detail below, area event detections can be combined with the half-wave event detections, line-length event detections, as well as any other applicable detection criteria described herein.

In one variation, each threshold for each channel and each analysis tool can be programmed separately. ("Tool" as used herein refers to an aspect of a unit, for example, the window analysis unit includes the line length analysis tool and the area analysis tool.) Therefore, a large number of individual thresholds may be used in the method for monitoring physiological information relating to sleep with an implantable device 110. It should be noted thresholds can vary widely and they can be changed and/or updated by a physician to meet the needs of an individual patient via the external programmer 312 (FIG. 3), and some analysis unit thresholds (e.g., line length and area) can also be automatically varied depending on observed trends in the data. This is preferably accomplished based on a moving average of a specified number of window observations of line length or area, adjusted as desired via a fixed offset or percentage offset, and may compensate to some extent for diurnal and other normal variations in brain electrophysiological parameters.

The methods described by the flow charts of FIGS. 11-13, 15-16, and 18-19 can be implemented in different ways. For example, state machines, software, hardware (including ASICs, FPGAs, and other custom electronics), and various combinations of software and hardware, are all solutions that would be possible to practitioners of ordinary skill in the art of electronics and systems design. Since minimizing the computational load on the processor is often desirable, certain operations can be implemented using hardware or a combination of hardware and software, rather than software alone.

As described previously in connection with FIG. 13, one of the detection schemes set forth above (i.e., half wave detection) is adapted to use an X-of-Y criterion to weed out spurious detections. This can be implemented via a shift register or, alternatively, by more efficient computational methods. Half waves can be analyzed on a window-by-window basis, and the window results can be updated with respect to a separate analysis window interval. If the detection criterion (i.e., a certain number of half waves in less than a specified time period) is met for any of the half waves occurring in the most recent window, then detection is satisfied within that window. If that occurs for at least X of the Y most recent windows, then this indicates that the half wave detection sought was, in fact, detected. If desired, X-of-Y criterion can be used with other detection algorithms (such as line length and area such that if thresholds are exceeded in at least X of the Y most recent windows, then the corresponding analysis unit triggers a detection. Also, in the described variations, each detection flag, after being set, remains set for a selected amount of time, allowing them to be combined by Boolean logic (as described below) without necessarily being simultaneous.

As indicated above, each of the software processes set forth above (FIGS. 12-13, 16, and 19) correspond to functions performed by the wave morphology analysis units 712 and window analysis units 714. Each one is initiated periodically, typically once per a window with a length that is predetermined (1212, 1512). The outputs from the half wave and window analysis units 712 and 714, namely the flags generated in response to counted qualifying half waves, accumulated line lengths, and accumulated areas, are combined to identify event detections as functionally illustrated in FIG. 8 and as described via flow chart in FIG. 20.

The process begins with the receipt of a timer interrupt (2010), which is typically generated on a regular periodic basis to indicate the edges of successive time windows. Accordingly, in a method according to the disclosed embodiment of the invention, such a timer interrupt is received every 128 ms, or as otherwise programmed or designed. Then the latest data from the half wave (2012, FIGS. 12-13), line length (2014, FIG. 16), and area (2016, FIG. 19) detection processes are evaluated, via the half-wave analysis flag, the line-length flag, and the area flag for each active sensing channel. The steps of checking the analysis tools (2012, 2014, and 2016) can be performed in any desired order or in parallel, as they are generally not interdependent. It should be noted that the foregoing analysis tools should be checked for every active channel (i.e., channels on which data is currently being sensed and/or processed), and may be skipped for inactive channels (i.e., detection channels not currently in use).

Figure 20:
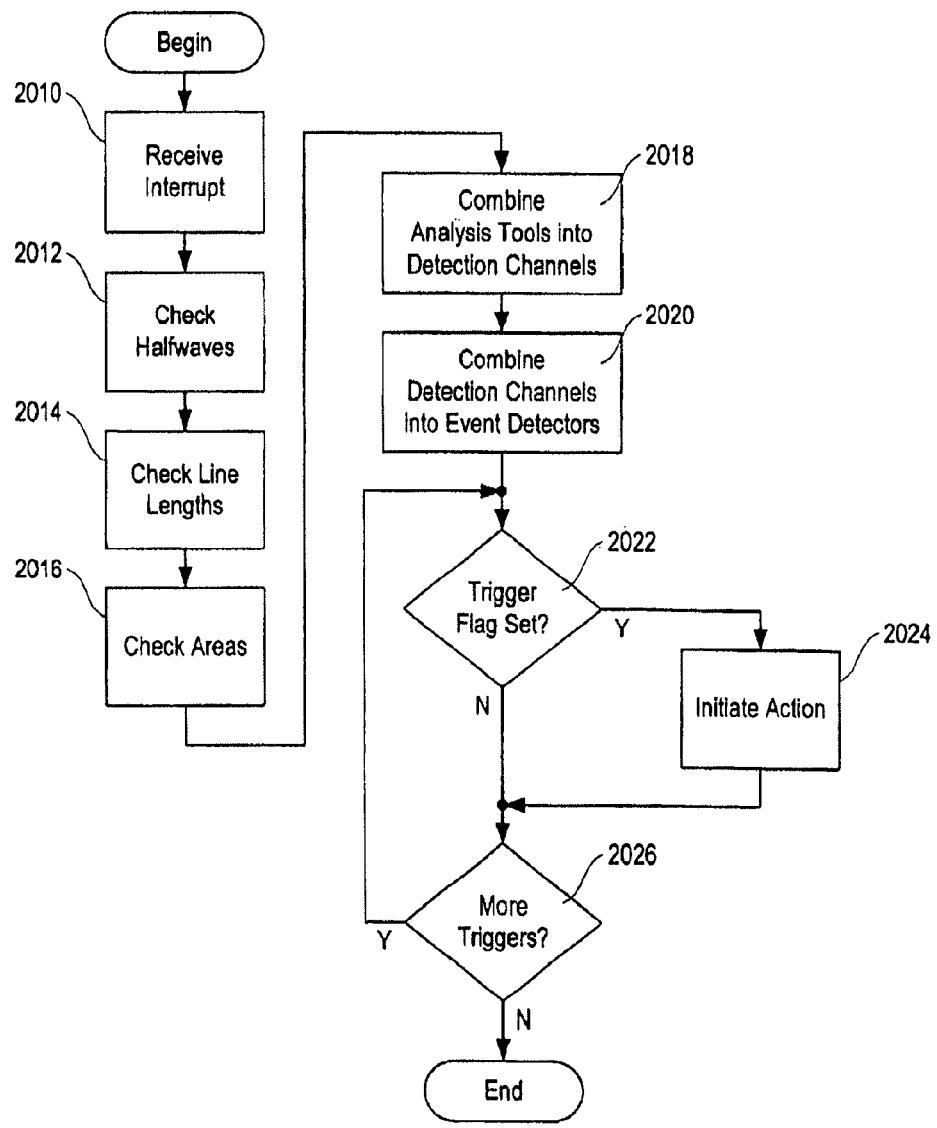
FIG. 20 is a flow chart of a method of analyzing half wave, line length, and area information using an event-driven feature of the central processing unit.

Flags that indicate whether particular signal characteristics have been identified in each active channel for each active analysis tool are then combined into detection channels (2018) as illustrated in FIG. 8. This operation is performed as described in detail below with reference to FIG. 21. Each detection channel is a Boolean "AND" combination of analysis tool flags for a single channel, and as disclosed above, there may be at least eight channels. The flags for multiple detection channels are then combined into event detector flags (2020), which are indicative of identified neurological events calling for action by the device. As shown in FIG. 20, if an event detector flag is set (2022), then a corresponding action is initiated (2024) by the device. Actions according to the invention can include the presentation of a warning to the patient, an application of therapeutic electrical stimulation, a delivery of a dose of a drug, an initiation of a device mode change, or a recording of certain EEG signals. It will be appreciated that there are numerous other possibilities. It is preferred, but not necessary, for actions initiated by a device according to the invention to be performed in parallel with the sensing and detection operations that are described in detail herein. It should be recognized that the application of electrical stimulation to the brain may require suspension of certain of the sensing and detection operations, as electrical stimulation signals may otherwise feed back into the detection system 422 (FIG. 4), causing undesirable results and signal artifacts.

Multiple event detector flags are possible, each one representing a different combination of detection channel flags. If there are further event detector flags to consider (2026), those event detector flags are also evaluated (2022) and may cause further actions by the device (2024). It should be noted that, in general, actions performed by the device (as in 2024) may be in part dependent on a device state. For example, even if certain combinations of events do occur, no action may be taken if the device is in an inactive state.

Figure 21:
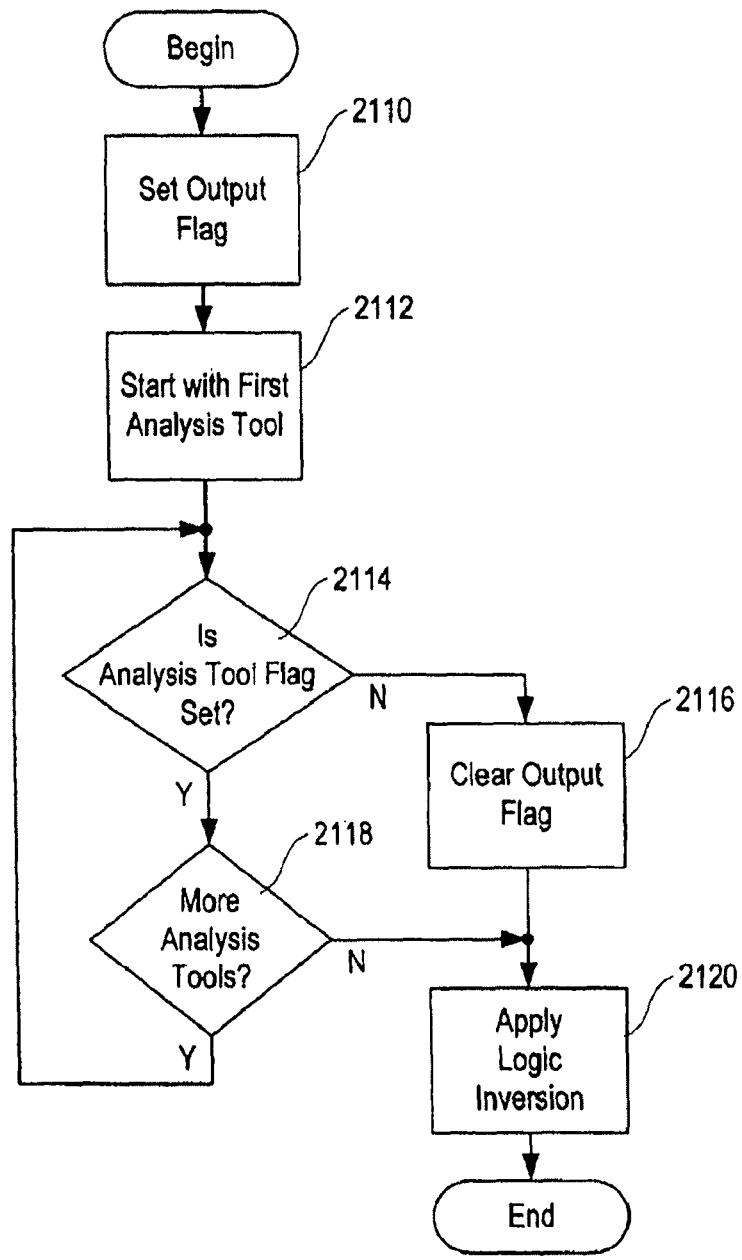
FIG. 21 is a flow chart of a method in which analytic tools are combined with a detection channel in an implantable device for monitoring physiological information relating to sleep.

As described above, and as illustrated in FIG. 20 as step 2018, a corresponding set of analysis tool flags is combined into a detection channel flag as shown in FIG. 21 (see also FIG. 8). Initially, the output detection channel flag is set (2110). Beginning with the first analysis tool for a particular detection channel (2112), if the corresponding analysis tool flag is not set (2114), then the output detection channel flag is cleared (2116).

If the corresponding analysis tool flag is set (2114), the output detection channel flag remains set, and further analysis tools for the same channel, if any (2118), are evaluated. Accordingly, this combination procedure operates as a Boolean "AND" operation. That is, if any of the enabled and active analysis tools for a particular detection channel does not have a set output flag, then no detection channel flag is output by the procedure.

An analysis tool flag that is cleared indicates that no detection has been made within the flag persistence period and, for those analysis tools that employ an X-of-Y criterion, that such criterion has not been met. In certain circumstances, it may be advantageous to also provide detection channel flags with logic inversion. Where a desired criterion (i.e., combination of analysis tools) is not met, the output flag is set (rather than cleared, which is the default action). This can be accomplished by providing selectable Boolean logic inversion (2120) corresponding to each event detector.

Figure 22:
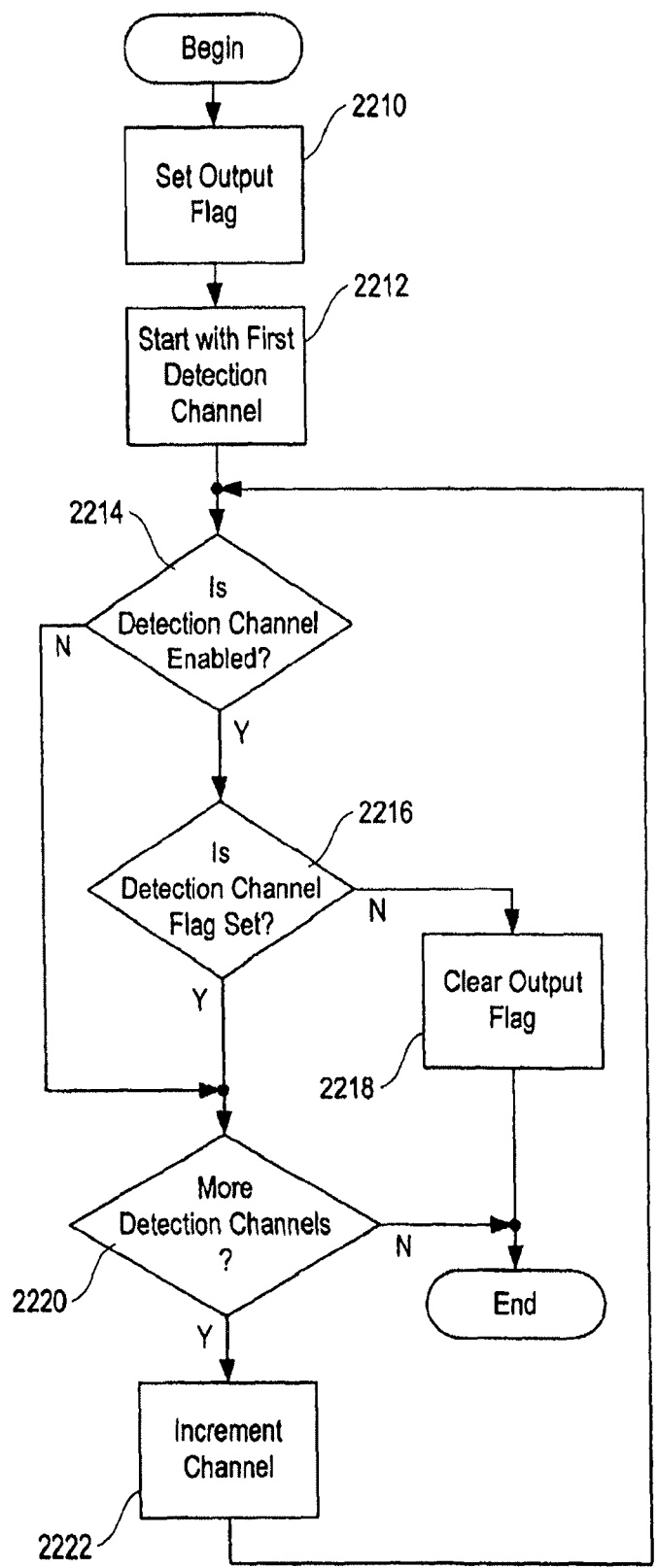
FIG. 22 is a flow chart of a method in which detection channels are combined in an event detector.

Also as described above, and as illustrated in FIG. 20 (2020), multiple detection channel flags are combined into a single event detector flag as shown in FIG. 22 (see also FIG. 8). Initially the output event detector flag is set (2210). Beginning with the first detection channel for a particular event detector (2212), if the channel is not enabled (2214), then no check is made. If the channel is enabled and the corresponding detection channel flag is not set (2216), then the output event detector flag is cleared (2218) and the combination procedure exits. If the corresponding detection channel flag is set (2216), the output event detector flag remains set, and further detection channels, if any (2220), are evaluated after incrementing the channel being considered (2222). This combination procedure also operates as a Boolean "AND" operation, as if none of the enabled and active detection channels has a set output flag, then no event detector flag is output by the procedure. It should also be observed that a Boolean "OR" combination of detection channels may provide useful information in certain circumstances. A software or hardware flow chart accomplishing such a combination is not illustrated, but could easily be created by an individual of ordinary skill in digital electronic design or computer programming.

In general, two different data reduction methodologies may be used in sleep state or stage detection. Both methods collect data representative of EEG signals within a sequence of uniform time windows each having a specified duration. The first data reduction methodology involves the calculation of a "line length function" for an EEG signal within a time window. Specifically, the line length function of a digital signal represents an accumulation of the sample-to-sample amplitude variation in the EEG signal within the time window. Stated another way, the line length function is representative of the variability of the input signal. A constant input signal will have a line length of zero (representative of substantially no variation in the signal amplitude), while an input signal that oscillates between extrema from sample to sample will approach the maximum line length. It should be noted that while the line length function has a physical-world analogue in measuring the vector distance traveled in a graph of the input signal, the concept of line length as treated herein disregards the horizontal (X) axis in such a situation. The horizontal axis herein is representative of time which, mathematically is not currently believed to be combinable in any meaningful way with information relating to the vertical (Y) axis, generally representative of amplitude, and which in any event would not be expected to contribute anything of interest The second data reduction methodology involves the calculation of an "area function" represented by an EEG signal within a time window. Specifically, the area function is calculated as an aggregation of the EEG's signal total deviation from zero over the time window, whether positive or negative. The mathematical analogue for the area function defined above is the mathematical integral of the absolute value of the EEG function (as both positive and negative signals contribute to positive area). Once again, the horizontal axis (time) makes no contribution to accumulated energy as treated herein. Accordingly, an input signal that remains around zero will have a small area value, while an input signal that remains around the most positive or most negative values will have a high area value.

Both the area and line length functions may undergo linear or nonlinear transformations. An example would be to square each amplitude before summing it in the area function. This nonlinear operation would provide an output that would approximate the energy of the signal for the period of time it was integrated. Similarly, linear and nonlinear transformations of the difference between sample values are advantageous in customizing the line length function to increase the effectiveness of the implantable device for a specific patient.

The central processing unit receives the line length function and area function measurements performed by the detection subsystem, and is capable of acting based on those measurements or their trends. Feature extraction, specifically the identification of half waves in an EEG signal, also provides useful information.

The identification of half waves having specific amplitude and duration criteria allows some frequency-driven characteristics of the EEG signal to be considered and analyzed without the need for computationally intensive transformations of time-domain EEG signals into the frequency domain. Specifically, the half wave feature extraction capability of the implantable devices described herein identifies those half waves in the input signal having a duration that exceeds a minimum duration criterion but do not exceed a maximum duration criterion, and an amplitude that exceeds a minimum amplitude criterion but do not exceed a maximum amplitude criterion. The number of half waves in a time window meeting those criteria is somewhat representative of the amount of energy in a waveform at a frequency below the frequency corresponding to the minimum duration criterion. Additionally, the number of half waves in a time window is constrained somewhat by the duration of each half wave (i.e., if the half waves in a time window have particularly long durations, relatively fewer of them will fit into the time window). That is, that number is highest when a dominant waveform frequency most closely matches the frequency corresponding to the minimum duration criterion.

As stated above, the half waves, line length function, and area function of various EEG signals can be calculated by customized electronics modules with minimal involvement by the central processing unit, and are selectively combined in the implantable device to provide detection and prediction of seizure activity, so that appropriate action can then be taken.

A number of other more sophisticated signal processing tools may be included in the device design in order to better detect sleep stages. For example, implementing a Fast Fourier transform (FFT) routine in the implantable device would allow a direct measure of the power spectrum over time. Thresholds for power within each low frequency band of interest could be set to identify different stages of sleep. Information related to theoretic measures such as entropy can also be used to measure different stages of sleep, as the signal's complexity is inversely correlated with the sleep depth. In addition, synchrony and mutual information between channels can be used as a measure for determining sleep stages, as these features have been shown to increase with the depth of sleep.

Other analytical methods for monitoring physiological information relating to sleep include developing individualized detection sets that are based on each individual patient's EEG signals. This is important because the underlying neurophysiological signals may vary from patient to patient due to electrode location, disease, or pharmacological effects. To implement an individualized detection set, the device may include algorithms for training a model based on artificial neural networks (ANN) or by using Hidden Markov Modeling. This analytical method would require additional input from the user (e.g., the patient's physician or clinician), including a training set of signals that have already been characterized by the user.

Physiological information other than EEG or ECoG signals may be used to provide supplementary information for sleep staging or, in the absence of EEG and/or ECoG data, as the primary information for sleep staging. For example signals from an intracranial sensor that monitors of global cerebral blood flow (CBF) and/or cerebral metabolic rate (CMR) can be incorporated into the implantable device. Global CBF and CMR are reduced during light sleep (Stage 2) compared to wake (3-10%), and even further reduced during deep sleep (25-44%). In addition, if the CBF/CMR sensors are place appropriately, localized information about CBF and CMR can be used to monitor the patient's state. Other implementations may include temperature, heart rate, position (including head position), EMG, EOG, and body movement sensors.

Data about low-frequency detections and sleep stages will be available to the physician when the device is interrogated. In addition, detections may be used to dynamically update therapy parameters in order to adjust therapy based on the patient's sleep schedule and/or to adjust therapy based on the patient's sleep state.

Sleep Staging Applications

Sleep stage information derived from the implantable device may be used to determine the effectiveness of sleep therapies and/or modulate therapy delivery (e.g., the implantable device may be programmed to deliver a different therapy during sleep and wake or during different sleep stages). In one variation, therapy may be coordinated with the detection of a particular sleep stage. For example, cardiac therapy may be implemented during a specific vulnerable sleep stage to reduce the occurrence of arrhythmia or ischemia. This information may also provide the patient, physician, or caretaker with information about the patient's sleep quality (e.g., duration of time to fall asleep, number of arousals from sleep, duration of time in slow-wave sleep periods, and duration of sleep cycles). A sleep quality index may also be generated to indicate sleep quality. The sleep quality index may be determined from a number of outputs derived from the sleep staging tools, including total duration of sleep within per 24 hours, the number of arousals per night, and the duration spent in each sleep stage.

The sleep stage information detected by the implantable devices herein described may also be used to treat various medical conditions (allocate therapy). For example, it may be used to treat neurological, psychological, cardiac, respiratory, and sleep conditions, or a combination thereof. Specific neurological conditions may include chronic pain, epilepsy, and movement disorders such as Parkinson's disease, Tourette's disorder, tremor, and restless leg syndrome. Psychiatric conditions such as depression, anxiety, and bipolar disorder may also be treated. Furthermore, the implantable devices may be used in methods of treating sleep conditions such as sleep apnea and narcolepsy.

For example, in epilepsy, some seizures occur preferentially during the drowsy state (Stage 1) or slow-wave sleep (Stage 3 and Stage 4). Therefore, the sleep staging detections may be used to modulate delivered therapy. For example, high frequency stimulation may be delivered in response to paroxysmal events during Stage 3 and Stage 4 sleep, while low frequency stimulation may be delivered during Stage 2 sleep, wake, and REM sleep, when seizures are less likely to occur.

Similarly, sleep disturbances and or disruptions are often associated with depression. An implantable sleep staging device may be used to monitor sleep disruptions and provide feedback to the physician about the patient's sleep quality as another metric of the patient's overall health. In addition, there is often a circadian mood cycle with depression, and an implantable device that could detect sleep stages may be used to allocate therapy in accordance to the patient's circadian cycle. For example, in patients who have worsening of mood in the morning, increased therapy may be provided in response to the detection of Stage 1 or the transition from Stage 1 to wake. This may be preferable to a scheduled increase in therapy dosage since patients may follow a different sleep routine from day to day. In addition to treating the mood symptoms, stimulation or drug therapy may also be provided in response to different sleep stages in order to better regulate sleep.

In another example, with movement disorders such as Parkinson's disease and essential tremor, an implantable device as described herein can be used as a sleep staging detector in conjunction with an implantable stimulator in order to regulate the amount of stimulation a patient receives during sleep. In some cases, stimulation may be turned off or greatly reduced when Stage 3 or Stage 4 sleep is detected. Limiting or reducing stimulation when it is not necessary can increase the battery life of the stimulator.

All publications, patents, and patent applications cited herein are hereby incorporated by reference in their entirety for all purposes to the same extent as if each individual publication, patent, or patent application were specifically and individually indicated to be so incorporated by reference. Although the foregoing implantable devices and their methods of use have been described in some detail by way of illustration and example for purposes of clarity of understanding, it will be readily apparent to those of ordinary skill in the art, in light of the description herein provided, that certain changes and modifications may be made thereto without departing from the spirit and scope of the appended claims.

What is claimed is:

1. A method of detecting a sleep state or sleep stage with an active implantable medical device, said method comprising:

determining first and second parameters of each of a plurality of half waves resulting from sensed physiological information;

for each of the plurality of half waves, determining that the half wave is a qualified half wave when the first parameter of the half wave satisfies a first criterion and the second parameter of the same half wave satisfies a second criterion, wherein each of the first criterion and the second criterion are defined by a respective minimum parameter and a respective maximum parameter;

counting a number of qualified half waves that occur during a time window; and detecting a particular sleep state or stage when a measure derived from the number satisfies a third criterion indicative of the particular sleep state or stage.

2. The method of claim 1, wherein:
the first parameter is a half-wave amplitude;
the minimum parameter of the first criterion is a minimum amplitude and the maximum parameter of the first criterion is a maximum amplitude; and
the first criterion is satisfied when a half-wave amplitude is between the minimum amplitude and the maximum amplitude.

3. The method of claim 1, wherein:
the second parameter is a half-wave duration;
the minimum parameter of the second criterion a minimum duration and the maximum parameter of the first criterion is a maximum duration; and
the second criterion is satisfied when a half-wave duration is between the minimum duration and the maximum duration.

4. The method of claim 1, wherein:
the measure derived from the number is an unsigned integer;
the third criterion is a threshold; and
the particular sleep state or stage is detected when the unsigned integer exceeds the threshold.

5. The method of claim 1, wherein:
the measure derived from the number is an unsigned integer;
the third criterion is one of a range of unsigned integers; and
the particular sleep state or stage is detected when the unsigned integer falls within the range.

6. The method of claim 1, wherein counting a number comprises:
classifying each qualified half wave as one of a plurality of half-wave types; and
for each of the plurality of half-wave types, determining a half-wave-type number corresponding to the number of qualified half waves classified as the half-wave type.

7. The method of claim 6, wherein:
the measure derived from the number is a ratio of two of the half-wave type numbers;
the third criterion is a threshold; and
the particular sleep state or stage is detected when the ratio satisfies the threshold.

8. The method of claim 6, wherein the plurality of half-wave types comprises at least two of the following half-wave types: alpha half-wave, delta half-wave and theta half-wave.

9. The method of claim 1, wherein the particular sleep state or stage includes stage 1 sleep, stage 2 sleep, stage 3 sleep or stage 4 sleep.

10. An active implantable medical device for detecting a sleep state or sleep stage, said device comprising:
a sensor configured to sense physiological information; and
a processor connected to the sensor and configured to:
determine first and second parameters of each of a plurality of half waves resulting from sensed physiological information;
for each of the plurality of half waves, determine that the half wave is a qualified half wave when the first parameter of the half wave satisfies a first criterion and the second parameter of the same half wave satisfies a second criterion, wherein each of the first criterion and the second criterion are defined by a respective minimum parameter and a respective maximum parameter;
count a number of qualified half waves that occur during a time window; and
detect a particular sleep state or stage when a measure derived from the number satisfies a third criterion indicative of the particular sleep state or stage.

11. The device of claim 10, wherein:
the first parameter is a half-wave amplitude;
the minimum parameter of the first criterion is minimum amplitude and the maximum parameter of the first criterion is a maximum amplitude; and
the first criterion is satisfied when a half-wave amplitude is between the minimum amplitude and the maximum amplitude.

12. The device of claim 10, wherein:
the second parameter is a half-wave duration;
the minimum parameter of the second criterion a minimum duration and the maximum parameter of the first criterion is a maximum duration; and
the second criterion is satisfied when a half-wave duration is between the minimum duration and the maximum duration.

13. The device of claim 10, wherein:
the measure derived from the number is an unsigned integer;
the third criterion is a threshold; and
the particular sleep state or stage is detected when the unsigned integer exceeds the threshold.

14. The device of claim 10, wherein:
the measure derived from the number is an unsigned integer;
the third criterion is one of a range of unsigned integers; and
the particular sleep state or stage is detected when the unsigned integer falls within the range.

15. The device of claim 10, wherein to count a number, the processor is configured to:
classify each qualified half wave as one of a plurality of half-wave types; and
for each of the plurality of half-wave types, determine a half-wave-type number corresponding to the number of qualified half waves classified as the half-wave type.

16. The device of claim 15, wherein:
the measure derived from the number is a ratio of two of the half-wave type numbers;
the third criterion is a threshold; and
the particular sleep state or stage is detected when the ratio satisfies the threshold.

17. The device of claim 15, wherein the plurality of half-wave types comprises at least two of the following half-wave types: alpha half-wave, delta half-wave and theta half-wave.

18. The device of claim 10, wherein the particular sleep state or stage includes stage 1 sleep, stage 2 sleep, stage 3 sleep or stage 4 sleep.

* * * * *